US012605527B2

(12) United States Patent
Baid

(10) Patent No.: US 12,605,527 B2
(45) Date of Patent: Apr. 21, 2026

(54) INTRAVENOUS CATHETER ASSEMBLY

(71) Applicant: POLY MEDICURE LIMITED, Faridabad-Haryana (IN)

(72) Inventor: Rishi Baid, New Delhi (IN)

(73) Assignee: POLY MEDICURE LIMITED, Faridabad-Haryana (IN)

( * ) Notice: Subject to any disclaimer, the term of this patent is extended or adjusted under 35 U.S.C. 154(b) by 57 days.

(21) Appl. No.: 16/604,413

(22) PCT Filed: Mar. 5, 2019

(86) PCT No.: PCT/IB2019/051757
§ 371 (c)(1),
(2) Date: Oct. 10, 2019

(87) PCT Pub. No.: WO2019/135208
PCT Pub. Date: Jul. 11, 2019

(65) Prior Publication Data
US 2020/0121896 A1 Apr. 23, 2020

(30) Foreign Application Priority Data

Mar. 5, 2018 (IN) .............................. 201811008072

(51) Int. Cl.
*A61M 25/06* (2006.01)
*A61M 25/00* (2006.01)
*A61M 39/06* (2006.01)

(52) U.S. Cl.
CPC .... *A61M 25/0625* (2013.01); *A61M 25/0097* (2013.01); *A61M 25/0606* (2013.01); *A61M 39/06* (2013.01)

(58) Field of Classification Search
CPC .......... A61M 25/0625; A61M 25/0618; A61M 25/0097; A61M 25/0606; A61M 5/32
See application file for complete search history.

(56) References Cited

U.S. PATENT DOCUMENTS 2,737,949 A * 3/1956 Brown .............. A61M 5/31595
604/243
2,745,403 A * 5/1956 Goldberg ................ A61M 5/24
604/206
(Continued)

FOREIGN PATENT DOCUMENTS

EP       2762193 A1   8/2014
GB       2508466 A    6/2014
(Continued)

OTHER PUBLICATIONS

International Search Report issued in PCT Application No. PCT/IB2019/051757 dated Aug. 30, 2019.
(Continued)

*Primary Examiner* — William R Carpenter
(74) *Attorney, Agent, or Firm* — Bradley Arant Boult Cummings LLP; Henry B. Ward, III

(57) ABSTRACT

An intravenous catheter assembly (410) comprising: a catheter tube (414); a catheter hub (412) having a distal end (422) and a proximal end (424), wherein the distal end (424) is joined to the catheter tube (414) and the proximal end (424) defines a housing (448) having inner space (467); a needle (420) extending through the catheter hub (412) and the catheter tube (414) and defining an axial direction (A), wherein the needle (420) has opposite proximal and distal ends, the distal end forming a needle tip (454); a port (464) extending outwardly in a direction perpendicular to the axial direction (A) from a sidewall (470) of the catheter hub (412); a needle hub (416) attached to the proximal end of the needle (420); a first valve (471) provided in the inner space (467) in the catheter hub (412) to prevent foreign contamination from entering the catheter hub (412); a blood control second valve (473) arranged within the inner space (467) of catheter hub (412) to prevent the outflow of fluid during and following removal of the needle (420) wherein the second valve
(Continued)

(473) configured with a plug (475) also housed in the inner space (467) of the catheter hub (412).

2 Claims, 21 Drawing Sheets

(56)                    References Cited

U.S. PATENT DOCUMENTS

| | | | | |
|---|---|---|---|---|
| 3,330,004 | A * | 7/1967 | Cloyd | B29C 45/14311 |
| | | | | 72/457 |
| 3,470,604 | A * | 10/1969 | Zenick | A61M 5/343 |
| | | | | 264/249 |
| 4,000,739 | A * | 1/1977 | Stevens | A61M 25/0662 |
| | | | | 604/537 |
| 4,266,543 | A * | 5/1981 | Blum | A61B 5/150282 |
| | | | | 600/576 |
| 4,430,081 | A | 2/1984 | Timmermans | |
| 4,809,679 | A | 3/1989 | Shimonaka et al. | |
| 5,102,395 | A | 4/1992 | Cheer et al. | |
| 6,024,729 | A | 2/2000 | Dehdashtian et al. | |
| 6,117,108 | A * | 9/2000 | Woehr | A61M 25/0625 |
| | | | | 604/110 |
| 6,234,999 | B1 * | 5/2001 | Wemmert | A61M 25/0625 |
| | | | | 604/162 |
| 6,623,458 | B2 * | 9/2003 | Woehr | A61M 5/3273 |
| | | | | 604/192 |
| 8,016,791 | B2 | 9/2011 | Sugiki et al. | |
| 9,345,862 | B2 * | 5/2016 | Baid | A61M 25/0618 |
| 10,449,331 | B2 | 10/2019 | Lim et al. | |
| 2001/0027298 | A1 * | 10/2001 | Vojtasek | A61M 25/0618 |
| | | | | 604/263 |
| 2006/0264833 | A1 * | 11/2006 | Moulton | A61M 25/0606 |
| | | | | 29/458 |
| 2007/0038186 | A1 * | 2/2007 | Sutton | A61M 25/0618 |
| | | | | 604/110 |
| 2007/0270754 | A1 * | 11/2007 | Soderholm | A61M 25/0625 |
| | | | | 604/110 |
| 2007/0270758 | A1 * | 11/2007 | Hanner | A61M 25/0625 |
| | | | | 604/177 |
| 2008/0082082 | A1 | 4/2008 | Carlyon et al. | |
| 2008/0243086 | A1 * | 10/2008 | Hager | A61M 25/0625 |
| | | | | 604/198 |
| 2009/0012476 | A1 | 1/2009 | Catlin | |
| 2009/0012479 | A1 | 1/2009 | Moller et al. | |
| 2010/0280455 | A1 * | 11/2010 | Ogawa | A61M 25/0637 |
| | | | | 604/164.01 |
| 2013/0090609 | A1 | 4/2013 | Sonderegger et al. | |
| 2013/0178800 | A1 * | 7/2013 | Domonkos | A61M 25/0625 |
| | | | | 604/164.08 |
| 2013/0218082 | A1 | 8/2013 | Hyer et al. | |
| 2013/0245567 | A1 * | 9/2013 | Tremblay | A61M 5/321 |
| | | | | 604/263 |
| 2014/0276434 | A1 | 9/2014 | Woehr et al. | |
| 2014/0364809 | A1 * | 12/2014 | Isaacson | A61M 25/0606 |
| | | | | 604/164.08 |
| 2015/0238733 | A1 * | 8/2015 | bin Abdulla | A61M 25/0637 |
| | | | | 604/263 |
| 2017/0043135 | A1 * | 2/2017 | Knutsson | A61M 25/0097 |
| 2019/0160264 | A1 * | 5/2019 | Isaacson | A61M 39/0693 |

FOREIGN PATENT DOCUMENTS

| | | | | |
|---|---|---|---|---|
| WO | 00/12171 A1 | 3/2000 | | |
| WO | WO-2016142410 A1 * | 9/2016 | | A61M 25/0097 |

OTHER PUBLICATIONS

Written Opinion issued in PCT Application No. PCT/IB2019/051757 dated Aug. 30, 2019.

* cited by examiner

FIG 4B
FIG 4C
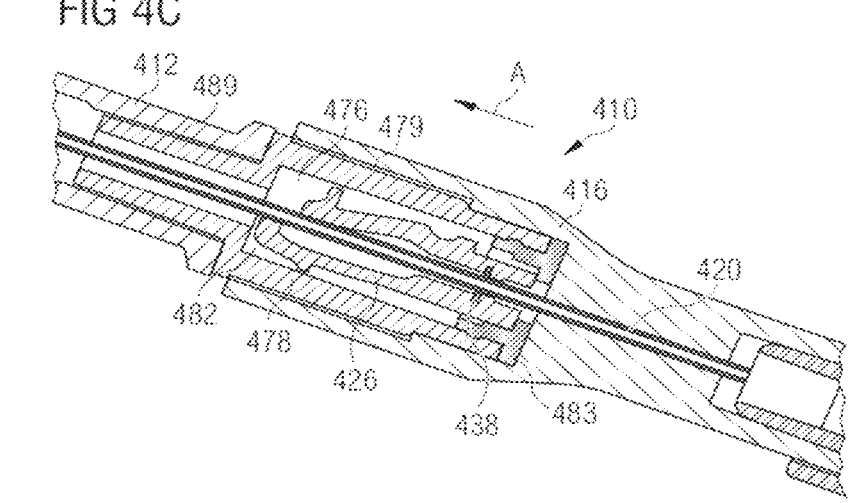
FIG 4D
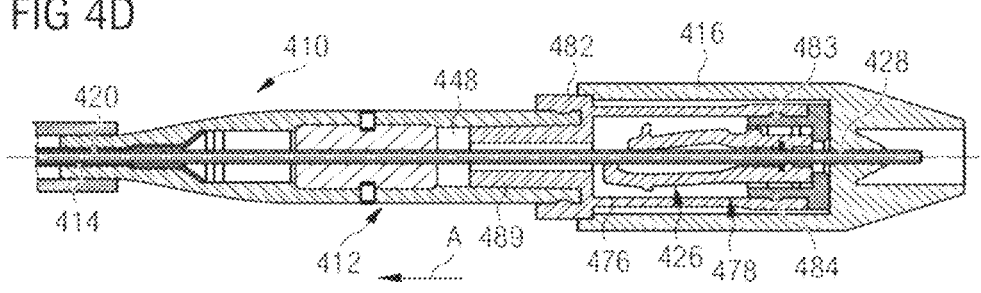

Y-Y
513
517  515  516  519  518  514

516
519

Y-Y
513
520

516

Y-Y
513
520

516

Y-Y

Y-Y

INTRAVENOUS CATHETER ASSEMBLY

FIELD OF THE INVENTION

The invention generally relates to intravenous catheter assemblies. More particularly, the invention relates to an intravenous catheter assembly comprising a catheter hub arranged at a proximal end of a catheter tube and having an inner space defining a housing; a needle having a needle tip attached to a needle hub having inner space defining a housing and extending through both the housings and the catheter tube when in a ready position.

BACKGROUND OF THE INVENTION

An intravenous catheter assembly of this kind is generally known. Catheter assemblies are used to place a catheter properly into the vascular system of a patient. Once in place, catheters such as intravenous ("IV") catheters may be used to infuse fluids including normal saline, medicinal compounds, and/or nutritional compositions or the like into a patient in need of such treatment. Catheters additionally enable the removal of fluids from the circulatory system and monitoring of conditions within the vascular system of the patient.

One type of commonly used catheter is a peripheral intravenous catheter which are indwelling intravenous catheters often used to provide an entry route for medications, fluid for hydration, and in some cases, for parenteral feeding, into a patient. Such catheters are generally short in length, ranging from about one-half to about three inches in length, and are generally made of flexible biocompatible materials. Peripheral intravenous catheters are often provided as "over-the-needle" catheters mounted over an introducer needle with a sharp distal tip. A portion of the catheter including at least the distal tip of the catheter securely grips the outside of the needle to prevent catheter peelback during insertion of the catheter into the circulatory system of the patient. Although several techniques for placing such catheters are practiced in the art, many generally include the step of inserting at least a portion of the needle into the target vessel and then sliding the catheter over the needle into place.

Once placement of the needle has been confirmed, the medical personnel may remove the needle, leaving the catheter in place. A septum within the catheter housing can prevent the outflow of fluid during and following removal of the introducer needle. These septum structures are generally elastomeric and are designed to closely conform to the shape of a needle during storage and use to prevent leaking, then to seal upon removal of the needle. However, if the needle is left within the septum for long periods, the septum may not completely seal after the needle is removed, having conformed, in part, to the shape of the withdrawn needle. An incompletely sealed septum can increase the risk of blood exposure to medical personnel, since blood may flow through the small opening in the slit of the septum. It would thus be an improvement in the art to provide a catheter assembly with more reliable sealing functionality. Such a catheter assembly is disclosed herein.

The catheter assembly is also provided with a needle guard slidably arranged on the needle and received in the housing when the needle is in its ready position, wherein the needle guard is configured to guard the needle tip upon withdrawal of the needle from the catheter hub.

The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

According to one of the embodiments of the invention, the catheter hub and/or needle hub within which the needle guard is received in a ready position includes holding means for holding the needle guard even under retracting forces acting on the needle guard when the needle is retracted out of the patient's vein. These holding means may include one or more depressions formed on the inner circumferential surface of the catheter hub and/or needle hub into which one or more protrusions formed on the first and second arm of the needle guard securely engages in the ready position. For example, when the first arm is deflected and spread apart from the second arm by the needle shaft.

SUMMARY AND OBJECTS OF THE INVENTION

A primary object and advantage of the present invention is to provide an improved intravenous catheter assembly which is inexpensive to manufacture, efficient, effective and simple in its construction and use.

It is another object of the present invention to provide an intravenous catheter assembly which provides better protection against accidental pricking by the needle tip and which is inexpensive to manufacture at the same time.

It is another object of the present invention to provide an intravenous catheter assembly with improved safety features having a needle guard slidably arranged on the needle and received in the hub when the needle is in its ready position, wherein the needle guard is configured to guard the needle tip upon withdrawal of the needle from the hub.

It is another object of the present invention to provide an intravenous catheter assembly which has better blood control features.

It is another object of the present invention to provide a compact design for housing one or more valves within the catheter hub housing of the intravenous catheter assembly having better blood control features.

According to one of the embodiments, the present invention relates to an intravenous catheter assembly comprising: a catheter tube; a catheter hub having a distal section and a proximal section, wherein the distal section is joined to the catheter tube and the proximal section defines a housing; a port provided on the catheter hub forming an opening into the inner space covered by a port cap, a needle extending through the catheter hub and the catheter tube and defining an axial direction, wherein the needle has opposite proximal and distal ends, the distal end forming a needle tip; a needle hub attached to the proximal end of the needle. The hub is also provided with wings which in use may be adhesively taped to the skin of the patient at the venipuncture site to maintain the device stationery during the infusion.

The port in the catheter assembly forms an opening into the inner space which can be covered by a port cap. In one of the embodiments, a first valve is provided adjacent to the port opening that provides selective access through the port. Fluid may be infused and withdrawn from the catheter through the port without the problem of leakage/outflow or risk of blood exposure. Thus, the port forms a first fluid path from the external environment into the inner space of the catheter assembly. The first valve provided in the first flow path further provides the ability to infuse and withdraw liquids through the port. Thus, the valve on or in the port provides a number of benefits when used with blood control-type catheter assemblies.

The catheter assembly is also provided with a second valve in the inner space which selectively seals a proximal end of the inner space of the catheter housing. Placing the second valve in the catheter hub avoids the problems of outflow of fluid for example, when the second valve is in the path of an introducer needle in the inner space of the catheter hub. The second valve is configured with a plug which is also housed in the inner space of the catheter hub.

Accordingly, in some implementations of the invention, the first valve adjacent to the port opening is utilized with a catheter assembly having an internal blood control second valve (also named second valve). The second valve can include a blood control septum. The blood control septum is provided to allow selective flow of fluid through the fluid pathway. For example, the blood control septum may include a slit that may be bypassed when an external luer device is coupled to the hub of the catheter assembly and directly engaging the septum. Upon removing the external luer device, the slit is closed to prevent blood from leaking out of the catheter assembly.

A septum activator may also be located within the inner space at a location that is behind the second valve. When a separate luer device is inserted into the proximal end of the catheter hub, the septum activator is advanced forward through the blood control septum of the second valve, activating the blood control septum. The septum activator generally comprises a tubular body that is rigid or semi-rigid. The tubular body further comprises an inner lumen for facilitating flow of a fluid and/or liquid through the septum activator. The distal end of the tubular body can be shaped and sized to compatibly enter within the one or more slits of the blood control septum of the second valve.

The valves provided can be of various types which can be incorporated into the port and the inner space in the catheter housing to provide medical personnel with the ability to infuse and withdraw fluids from the catheter assembly. The valve can be a one-way valve or a two-way valve. A two-way valve is a valve that permits fluid flow in two directions through or around the valve when the valve is open. Non-limiting examples of a two-way valve include a split septum, a ball valve, and an iris valve or the like. Thus, a two-way valve can permit fluid to be introduced into the catheter assembly (a first way) and to be withdrawn from the catheter assembly (a second way).

In some embodiments, the valve is a one-way valve, which is a valve that only permits substantial fluid flow in a single direction when the valve is open. A non-limiting example of a one-way valve is a check valve.

The valve can be housed inside the port or in the inner space provided in the housing of the catheter assembly. These valve types are not presented as an exhaustive set of valve types, and thus it will be understood that other suitable valves can be utilized in port and the catheter assembly.

In further embodiments of the invention, the first valve can be located on a removable luer access connector that can be connected and disconnected from the port. Alternatively, the first valve can be located on a luer access connector that is fixedly connected to the port. The first valve can be a luer access valve that accommodates the insertion of a luer device, such as those commonly used in the medical industry. Moreover, a body portion of the port can include luer threads or other connecting and/or fastening features that can secure a luer device to the catheter assembly.

In some configurations, the port can be disposed at an angle relative to the longitudinal axis of the catheter in order to modify the direction at which fluids are infused into the inner housing of the catheter assembly. This angle can be between about 10° to about 90°. The angle of the port can be modified to facilitate use, optimize performance, and/or optimize fluid flow within the inner space of the catheter assembly.

The embodiments of the present invention also include the provisions for including a needle guard slidably arranged on the needle, wherein the needle guard is movably retained in the housing of the catheter hub when the needle extends through the catheter hub and the catheter tube, and wherein the needle guard is removable from the catheter hub once the needle tip is received in the needle guard upon withdrawal of the needle from the catheter tube; and wherein the housing defines a chamber at one end thereof ensuring that a first and second arms of the needle guard do not engage or interact with an inner surface of the chamber prior and during venipuncture of a patient. An intravenous catheter assembly of this kind is generally known. The needle guard serves to prevent a person handling the intravenous catheter apparatus from accidentally coming into contact with the needle tip after placement of the catheter tube in and subsequent removal of the needle from a patient's vein. Thereby, the intravenous catheter assembly helps to avoid unwanted transmission of blood borne diseases.

As well known in the art, the needle may also have a needle feature close to its needle tip, which interacts with a proportional base of the needle guard, e.g. a curving or a bulge or crimp any other change in profile. Thereby, it can be prevented that the needle is retracted out of the needle guard, which is known in the art.

In an embodiment, the catheter hub is made of two parts. The first and second parts being joined together define the housing having an inner space. The first and second part may form the housing, in particular, the distal end section of the first part and the proximal end section of the second part may form the housing, which ensures that no undercut has to be formed in either one of the first and second part.

Further, the first part includes the port defining a first flow path. Alternatively, it is also possible to provide the port on the second part. The first and second parts of the catheter hub may be joined by complementary end portions, which preferably as such extend at an angle with regard to the axial direction. This ensures that both parts are aligned concentrically towards each other. Thereby, the assembly of such a catheter hub can be made easier. These end portions may be stepped, which enlarges their contact area for a better mutual interconnection.

In an embodiment, the inner space of the catheter hub may receive a needle guard which is movably arranged on the needle shaft. The chamber may be formed by an indentation in the housing for accommodating the first and second arm such that none of the arms deflected by the needle contacts an inner surface of the chamber. Through such indentation the overall outer dimensions of the housing and the catheter hub can be kept small, which it is still provided that the first arm and second arm of the needle guard do not contact the inner wall surface of the chamber.

The inner space of the housing may be parallel to the axial direction and defined by the distal end section of the first part and the proximal end section of the second part of the catheter hub. Alternatively, the inner space of the housing is defined only by one of the first or second part i.e. by either the distal end section of the first part or the proximal end section of the second part. Further alternatively, the inner space of the housing is defined by the proximal end section of the second part. The advantage in this lies in the fact that only one of the two parts forming the catheter hub has to be dimensioned very precisely in order to ensure an inner space with a well-controlled and large enough diameter such that none of the arms of the needle guard when housed in the inner space of the catheter hub contact said inner surface. In this regard, it is advantageous that the inner space of the housing is defined by the first and second part comprising the second fluid path.

According to one of the embodiments of the invention, one of the first or second part of the catheter hub comprises a surface joined with the inner surface of the one of the first or second part, which surface is inclined towards the inside of the housing in a proximal direction of the catheter hub, wherein the surface has a smaller inside diameter at its innermost end than a distance between outermost points of the arms in their deflected state inside the chamber. Preferably, the first part comprises the surface joined with the inner surface of the second part. Preferably, the distal end section of the first part comprises the surface joined with the inner surface of the proximal end section of the second part. Such a surface serves as a stop for the arms of the needle guard when housed in the inner space of the catheter hub in their deflected state such that they cannot be pulled out of the catheter hub in the proximal axial direction as long as the needle deflects them outward in the ready position of the needle guard. On the other hand, the inclination of the surface supports that the arms are directed inwards when the needle guard is pulled out in the retracted position, even if they have been plastically deformed by the needle in their deflected state.

In some embodiments, an antimicrobial coating is applied to one or more surfaces of the intravenous catheter assembly. The antimicrobial coating further includes an antimicrobial agent that is compatible for use in intravenous catheter assembly used for infusion therapy. Non-limiting examples of suitable antimicrobial agents include chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

Accordingly, one of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle; a first valve provided in the inner space in the catheter hub to prevent foreign contamination from entering the catheter hub; a blood control second valve arranged within the inner space of catheter hub to prevent the outflow of fluid during and following removal of the needle wherein the second valve configured with a plug also housed in the inner space of the catheter hub.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub a needle hub attached to the proximal end of the needle having a housing; a needle guard slidably arranged on the needle, wherein the needle guard is movably retained in a needle guard casing and the needle guard casing is movably retained in the housing of the needle hub, when the needle extends through the needle hub, catheter hub and the catheter tube, wherein the needle guard is removable from the needle hub being retained in the needle guard casing and then the needle tip is received in the needle guard upon withdrawal of the needle from the catheter tube.

One of the embodiments of the present invention relates to an intravenous catheter assembly comprising: a catheter tube; a catheter hub having a distal end and a proximal end, wherein the distal end is joined to the catheter tube and the proximal end defines a housing having inner space; a needle extending through the catheter hub and the catheter tube and defining an axial direction (A), wherein the needle has opposite proximal and distal ends, the distal end forming a needle tip; a port extending outwardly in a direction perpendicular to the axial direction (A) from a sidewall of the catheter hub; a needle hub attached to the proximal end of the needle having a housing; a needle guard slidably arranged on the needle and an upper end of the needle guard is securely retained in the housing of the catheter hub exposing the lower end of the needle guard and wherein in the ready to use position, the entire catheter hub portion with the lower end of the needle guard is securely retained in an inner space of the needle hub.

Some embodiments of the present invention further comprise one or more methods for manufacturing an intravenous catheter assembly according to the teachings of the instant invention. For example, in at least one embodiment a method of manufacturing is provided comprising the following steps: 1) providing catheter assembly having a catheter hub which has a proximal end, a distal end and an inner space extending therebetween; 2) placing a side port on a sidewall of the catheter hub and forming a pathway through the sidewall of the catheter hub and in communication with the inner space: 3) disposing a first valve within the inner space and forming a seal between the inner space and the pathway of the side port 4) disposing a blood control second valve within the inner space and dividing the inner space into a proximal chamber and a distal chamber. In some instances, a further step is provided for providing a needle guard for securely covering the needle tip once withdrawn from the patient in order to prevent accidental pricking. The needle guard can be housed in the catheter hub or the needle hub or in part within the catheter hub or in part within the needle hub or in part both within the catheter hub or needle hub or within a needle guard casing. Alternatively, a needle guard can be located outside of a catheter hub, such as in a separate hub different from the catheter hub and needle hub. The needle guard of the present disclosure may embody any number or type of prior art guards configured for blocking or covering the needle tip of the needle in protected position.

Some embodiments of the present invention further comprise a disc arranged proximate to the first valve, the second valve, or both the first and the second valve.

The disc can be configured to hold the valve in its position. The disc can be configured such that at a high pressure, the valve arranged proximate to the disc does not displace from its position.

Some embodiments of the present invention further comprise a cut in the proximal end of the catheter hub. The cut may support locking of the catheter hub with the needle hub. The cut may further restrict the rotation of the catheter hub with respect to the needle hub. The cut may also be configured to reduce the withdrawal force required to withdraw the needle hub from the catheter hub.

Some embodiments of the present invention further comprise a proximal needle feature at the proximal end, opposite to the needle tip end. The proximal needle feature can, in addition to needle fixation means, increase the force required to separate the needle from the needle hub.

Some embodiments of the present invention further comprise at least one wing alignment feature and/or at least one catheter alignment feature configured to align and orient the wing with the catheter hub. The at least one wing alignment feature and/or at least one catheter alignment feature can further be configured to prevent distal or proximal movement of the wings with respect to the catheter hub.

Some embodiments of the present invention further comprise at least one needle guard engaging element configured to restrict the rotation of the needle guard. The needle guard may comprise a corresponding needle guard anti-rotation element configured to engage the needle guard engaging element, Some embodiments of the present invention further comprise wing members made of a soft material, a rigid material, or a combination of a soft and a rigid material. The wings may further comprise a window configured for air venting.

Some embodiments of the present invention further comprise wings having a tapered profile. The tapered profile may have an increasing width in proximal direction. The tapered profile can support the alignment of the device with a patient's body and can support the insertion of the needle.

Some embodiments of the present invention further comprise a curved and/or tapered proximal end of the catheter hub. The curved and/or tapered proximal end may simplify assembly of the catheter hub with the needle hub.

Some embodiments of the present invention further comprise a port including a port hole, the port hole can contribute in directional flow of fluid through the port. The port hole profile and location can be changed and the specific position and design of the port hole can be configured to optimize the flow and pressure balance.

Some embodiments of the present invention may comprise a valve comprising an elastomeric member having a peripheral wall projecting from a base surface. The base surface can comprise at least one slit, which passes through the thickness of the base surface. The elastomeric member can have a lateral annular protrusion from edge of the base surface configured to be received by a recess (not shown) within an interior wall of the catheter hub. The lateral annular protrusion can support the holding of the valve in the catheter hub.

Some embodiments of the present invention may comprise an inner vertical projection extending from the base surface of the valve. The inner vertical projection may have a rounded shape. The base surface can include a second vertical projection extending from the vertical annular projection. The second vertical projection may have a smaller diameter than the vertical annular projection.

Some embodiments of the present invention may comprise a valve comprising at least one slit in the base surface. The valve can comprise at least one center slit, A center slit can support the introduction of the needle in the valve and can be configured to seal once the needle is withdrawn. The valve can comprise at least one outer slit. An outer slit can contribute towards aspiratory flow, for instance while drawing blood using a syringe. The valve can comprise at least one center slit and at least one outer slit. The center slit can have the form of a hole, a slit, a cross slit, a plus slit, a Y slit, an arc slit, a V slit, or any other shape. The center slit profile may vary with respect to the shape, size, or orientation of the slit. The center slit may be made in any way or process. The outer slit may have the form of a slit, a T slit, a Y slit, a V slit, a rounded V slit, an arc slit, or any other shape. The outer slit profile may vary with respect to the shape, size, orientation, location or number of the at least one slit. The at least one outer slit may be made in any way or process. The valve may comprise any combination of a central slit and outer slits.

BRIEF DESCRIPTION OF THE ACCOMPANYING DRAWINGS

The foregoing and other objects, features, and advantages of the invention will be apparent from the following detailed description taken in conjunction with the accompanying drawings, wherein:

FIG. 4B is a cross-sectional side view of the needle guard of the present invention.

FIG. 4C is a cross-sectional side view of the intravenous catheter assembly showing a catheter hub, a needle hub and a needle guard casing with a needle guard retained in the needle hub according to one of the embodiments of the present invention.

FIG. 4D is a cross-sectional side view of the intravenous catheter assembly showing a catheter hub, a needle hub and a needle guard casing with a needle guard retained in the needle hub according to one of the embodiments of the present invention.

FIGS. 17A, 17B, 17C, 17D, 17E, and 17F are views of different configurations of a valve that can be used in combination with any of the catheter assemblies described in the present invention.

FIGS. 18A, 18B 18C, 18D and 18E are views of slits of the valve that can be used in combination with any of the catheter assemblies described in the present invention.

Figure 19A:
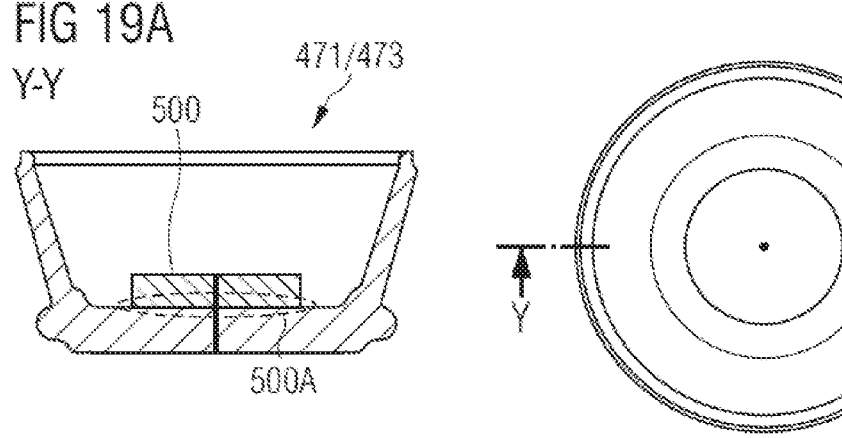
Figure 19B:
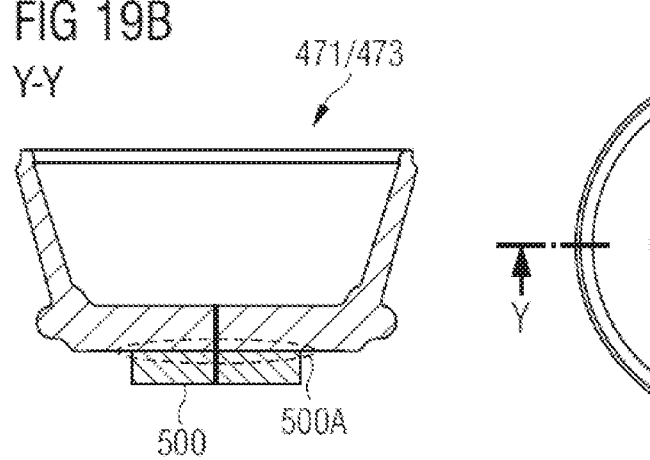
Figure 19B:
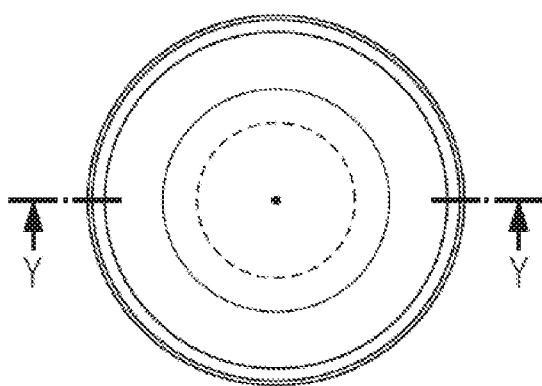

FIGS. 19A and 19B, are views of the disc being joint to the valve that can be used in combination with any of the catheter assemblies described in the present invention.

DETAILED DESCRIPTION OF THE INVENTION

Embodiments of the presently disclosed invention will now be described in detail with reference to the drawings wherein like reference numerals designate identical or corresponding elements. In the drawings and in the description, the term "proximal", "top", "up" or "upper" refers to a location on the device that is closest to the clinician using the device and farthest from the patient in connection with whom the device is used when the device is used in its normal operation. Conversely, the term "distal", "bottom", "down" or "lower" refers to a location on the device that is farthest from the clinician using the device and closest to the patient in connection with whom the device is used when the device is used in its normal operation. For example, the distal region of a needle will be the region of the needle containing the needle tip which is to be inserted e.g. into a patient's vein.

As used herein, the term "in" or "inwardly" or "inner" refers to a location with respect to the device that, during normal use, is the inside of the device. Conversely, as used herein, the term "out" or "outwardly" or "outer" refers to a location with respect to the device that, during normal use, is toward the outside of the device.

As used herein, the terms first, second, third, etc. are understood to describe different structures so as to distinguish one from another. However, the terms are not structurally limiting unless the context indicates otherwise.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

As used herein "ready position" means the catheter assembly is ready for use, such as to perform a venipuncture or intravenous access. Sometimes the ready position first requires removing a protective cap from the catheter assembly or needle assembly. The protective cap can be included for packaging.

As used herein "protected position" means the catheter assembly in particular the needle hub having a needle is ready for disposal in that the needle tip is safely guarded by a needle guard.

Figures 1, 2A, 2B, 2C:
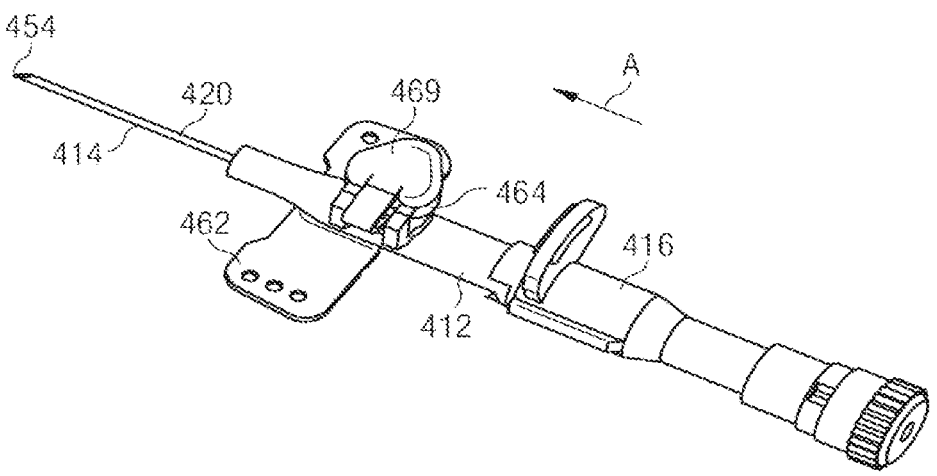
FIG. 1 illustrates an intravenous catheter assembly according to one of the embodiments of the present invention.
FIGS. 2A-2C are different embodiment of the needles according to the present invention.

Referring to FIG. 1 an intravenous catheter assembly 410 in accordance with one of the embodiments of the invention is illustrated. The intravenous catheter assembly 410 generally comprises various features and elements to enable intravenous infusion of a fluid or medicament into a patient. In some instances, intravenous catheter assembly 410 further comprises features to enable removal of a fluid from a patient, such as blood. The intravenous catheter assembly 410 includes a catheter hub 412 having a first fluid path 411a and a second fluid path 411b, a catheter tube 414 and a needle 420 attached to a needle hub 416. The catheter hub 412 has a distal end 422 and a proximal end 424, wherein the catheter tube 414 is arranged adjacent to the distal end 422 of the catheter hub 412, for instance with a slip ring 461. The catheter tube 414 can generally include a biocompatible material that is made of a flexible or a semi-flexible polymer. The catheter tube 414 and the catheter assembly 410 may be integrally coupled such that an inner space defining a housing 448 of the catheter hub 412 extends into the catheter tube 414. The catheter hub 412 may also be provided with wings 462 which in use may be adhesively taped to the skin of the patient at the venipuncture site to maintain the catheter assembly/device 410 stationery during the infusion.

Referring now to FIGS. 2A to 2C, the needle 420 has a needle shaft 428, a needle tip 454 at a distal section 463 of the needle shaft 428 and a needle hub 416 attached to a proximal section 436 of the needle shaft 428. An enlargement 496 of the needle 420 can be provided between the distal section 463 and the proximal section 436 of the needle shaft 428. The enlargement 496 can have a maximum dimension in a direction transverse to the needle shaft 428, which is greater than the outer diameter of the distal 463 or proximal section 436. The enlargement 496 can be made, for example, by crimping the needle shaft 428. The crimp may be made by a local depression 498 such that lateral protrusions/enlargement 496 result from the crimping process. The crimping process may be controlled such that the internal cross-sectional area of the needle 420 is not reduced substantially such that the through bore or the internal profile of the needle 420 is not affected. Prior to use of the catheter assembly 410, the needle 420 is received in the catheter hub 412 and catheter tube 414, such that the needle shaft 428 extends through the length of the catheter tube 414 and the needle tip 454 is exposed out of the catheter tip. The needle 420 is capable of piercing the skin to provide access to the vasculature or subcutaneous tissues of the patient. Once access is obtained, tip of catheter 414 is inserted through the newly formed opening and into the desired location within the patient. The needle 420 is then withdrawn from the catheter assembly 410, and catheter 414 is left disposed within the patient.

The needle 420 may comprise at least one opening 497 covered by the tubular catheter 414. The opening 497 can provide communication between a lumen of the needle 420 and an interior of the tubular catheter 414. In the event of first venipuncture blood entering the lumen of the needle 420 can exit the needle 420 through the opening 497 and thus become visible for the person handling. The opening 497 is preferably large enough in order to provide an early blood flashback function within the tubular catheter 414 such that the practitioner can recognize that he has placed the needle 420 correctly within a patient's vein. In case of a correct positioning of the needle 420, blood pours out of the opening 497 within the needle shaft 428 into the space between the needle shaft 428 and the inner wall of the transparent tubular catheter 414 and is visible to the practitioner. Preferably, the opening 497 is positioned close to the needle tip 454 so that the blood does not have to travel the length of the needle 420 to enter the needle hub 416 in order to become visible. Instead, blood entering the lumen of the needle 420 upon venipuncture partly exits the needle 420 near the needle tip 454, thereby becoming particularly quickly and, thus, allowing for particularly fast venipuncture confirmation. The opening 497 may have a miniscule size which serves the purpose of early flashback detection and which does not obstruct the arms of the needle guard 426.

The opening 497 can be provided before or after the enlargement 496. In further embodiments of the invention, the needle 420 may also be formed with the opening 497 arranged distally or proximally from the enlargement 496. The opening 497 may be formed by a small slit which is cut into the needle shaft 428 and which extends in axial direction A for about a small distance. The opening 497 may be just large enough in order to provide an early blood flashback function close to the needle tip 454 within the catheter tube 414 such that the practitioner can recognize that he has placed the needle 420 correctly within a patient's vein. In case of a correct positioning of the needle 420, blood pours out of the opening 497 within the needle shaft 428 into the space between the needle shaft 428 and the inner wall of the transparent catheter tube 414 and is visible to the practitioner.

Figure 3:
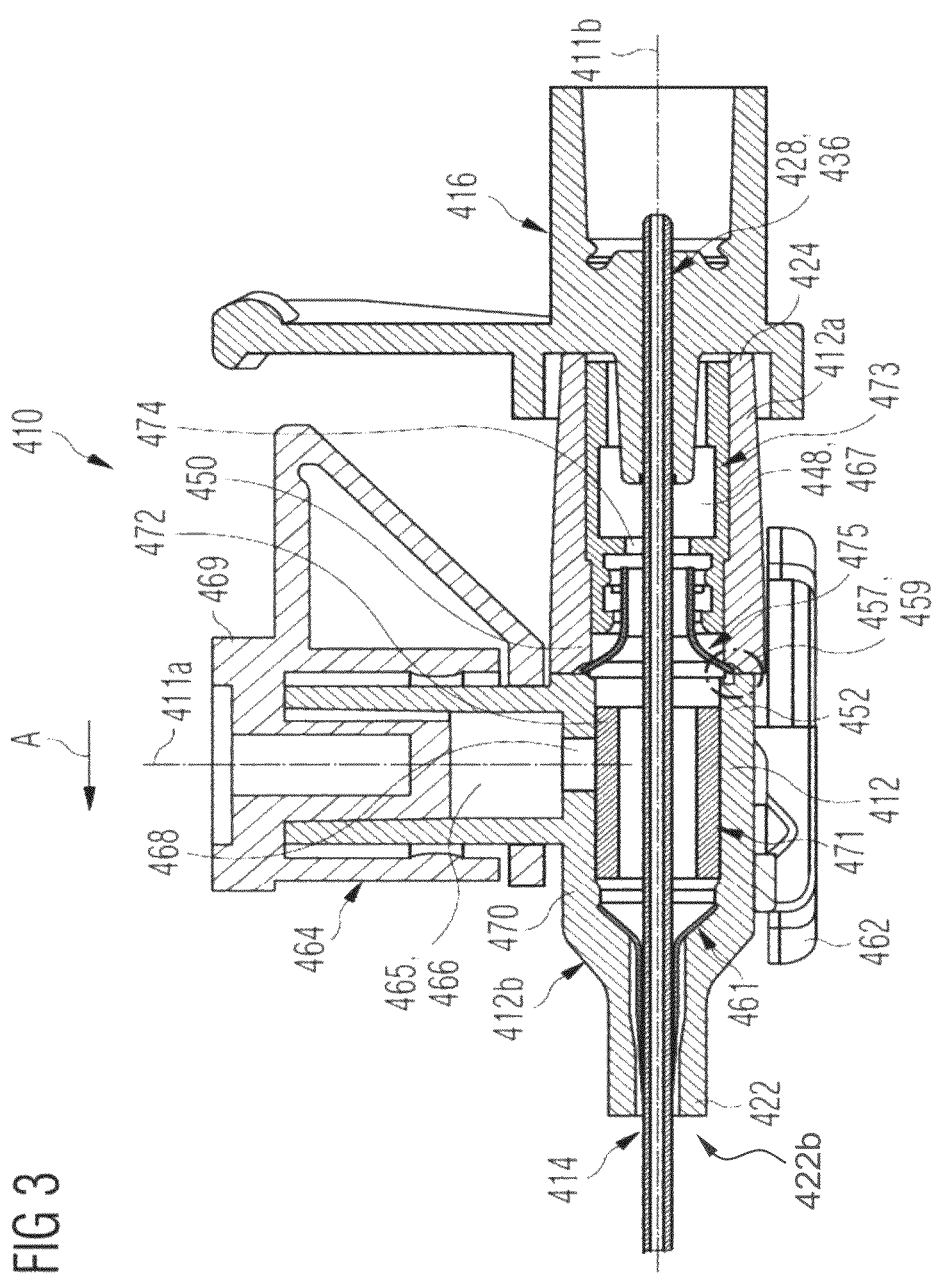
FIG. 3 is a cross-sectional side view of the two parts forming a catheter hub of the intravenous catheter assembly according to one of the embodiments of the present invention.

Referring now to FIG. 3, the catheter hub 412 is made of two parts, i.e. a first part 412a and a second part 412b. The first part 412a has a distal end section 450 and the second part 412b has a proximal end section 452. The distal end 422b of the second part 412b is connected to a catheter tube 414. The distal end section 450 of the first part 412a is configured to be assembled with the proximal end section 452 of the second part 412b in various ways in a fluid tight manner, such as by adhesive sealing, ultrasonic welding, heated die, radio frequency sealing, mechanical seal (snap fit), insert molding, laser welding etc., ensuring a leak free joint. It is also possible to join the two parts 412a, 412b to one another, for example, using threads, interference, or snap-fit. In particular, as can be seen in FIG. 3, the first and second parts 412a and 412b are joined by complementary stepped end portions/surfaces 457, 459.

A port 464 includes a port body having one or more integrated body portions which extend outwardly in a direction perpendicular to the axial direction A from the sidewall 470 of the catheter hub 412. The port 464 has an opening 465 defining an inlet and a bore 466 extending between the inlet and the opening 468 of the inner space 467 of the catheter hub 412. The port 464 and in particular, the inlet 465 and at least a portion of bore 466 is shaped and sized in conformity with the prescribed International Standards Organization (ISO) standards for a female luer connection. This will allow a male luer slip or male luer lock to be connected to port 464. The port 464 is covered with a port cap 469.

The port 464 can be a side port or a top port. Fluids may be infused and withdrawn from the catheter assembly 410 through the port 464 in a sidewall 470 of the catheter hub 412. The sidewall 470 can be any wall of the catheter hub 412 that extends substantially axially along the catheter tube 414.

In various embodiments, the outer periphery and/or inner periphery of the port 464 body can include one or more luer threads or the like in any number of thread configurations available to provide and interlock between mating devices. The luer threads allow another medical device having a male luer lock to be connected to and interlocked with the port 464. Alternatively, the port 464 body can also have no luer threads to accommodate luer slip and luer lock connections.

A first valve 471 may be provided in an inner space 467 adjacent to an inlet opening 468 in the catheter hub 412 to prevent foreign contamination from entering the catheter hub 412 that provides selective access through the port 464. The first valve 471 may include an elastomeric septum 472 having at least one slit that can form a fluid barrier until the septum deforms to allow fluid flow there through. Slit provides a fluid-tight seal, thereby preventing fluid from bypassing septum 472. The first valve 471 may generally comprise a flexible tube having an outer diameter that is approximately the same size as an inner diameter of the inner space 467 of the catheter hub 412, whereby the first valve 471 may be retained within the inner space 467 by an interference fit or by means of change of dimensions.

Figure 4A:
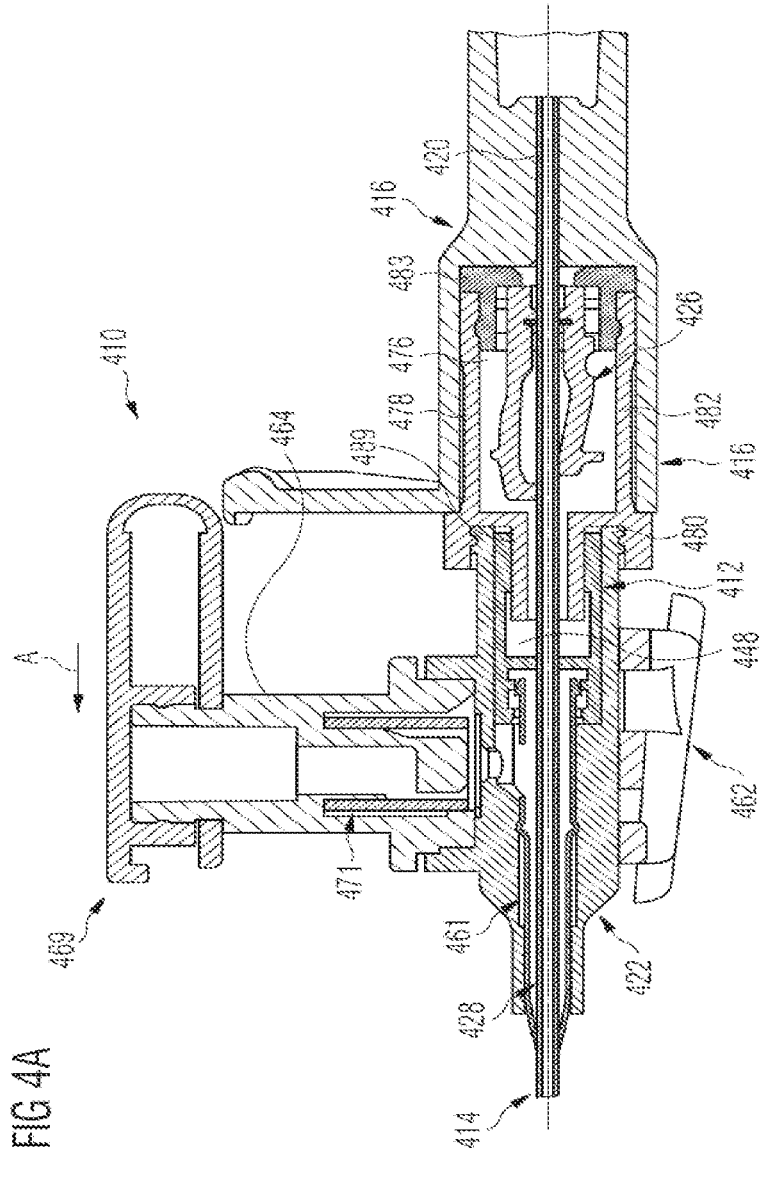
FIG. 4A is a cross-sectional side view of the intravenous catheter assembly showing a side port, a catheter hub, a needle hub and a needle guard casing with a needle guard retained in the needle hub according to one of the embodiments of the present invention.
Figure 5A:
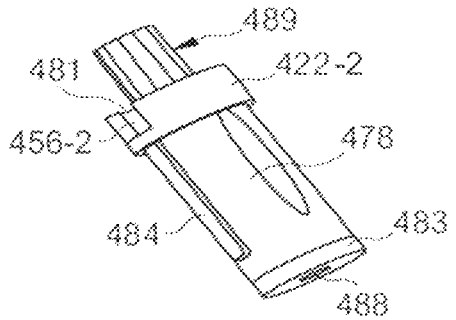
FIG. 5A is a perspective view of the needle guard casing of the present invention.
Figure 5B:
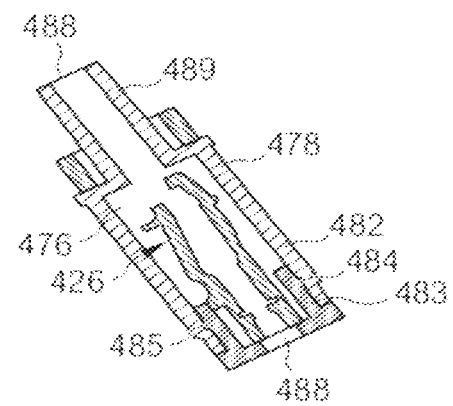
FIG. 5B is a cross-sectional side view of the needle guard casing showing a needle guard housed within according to one of the embodiments of the present invention.
Figure 5C:
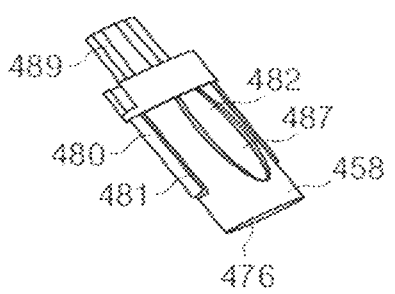
FIG. 5C is a perspective view of the upper part of the needle guard casing of the present invention.
Figure 5D:
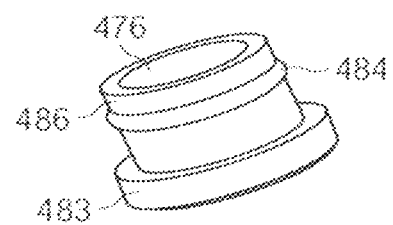
FIG. 5D is a perspective view of the lower part of the needle guard casing of the present invention.

The first valve 471 can be located on the inlet 465, within the inlet 465, adjacent to the inlet 465, within the bore 466 of the port body 464 or in the inner space 467 adjacent to the inlet opening 468 in the catheter hub 412. As shown in FIG. 4A, the first valve 471 is arranged within the bore 466 of the port body 464.

First valve 471 may generally comprise a resilient, flexible material that is easily deformed when fluid is introduced to port 464 via a syringe or other compatible device. Materials such as silicone, silicone rubber, or polyisoprene or the like can be used to form the first valve 471. The first valve 471 can be formed as a single piece of elastomeric material that is formed to having various shapes and features. Alternatively, the first valve 471 can be a two-piece configuration having a flexible inner material, such as silicon or silicone rubber, and a more rigid outer portion, such as an outer ring. The outer ring can be formed of a plastic or metal or other suitable material. The first valve 471 includes at least one slit. Alternatively, first valve 471 can include a plurality of slits. In some configurations, at least a portion of the first valve 471 is glued to the port body 464 using one or more adhesives in a fluid tight manner.

Additionally or alternatively, in some configurations, at least a portion of the first valve 471 is held in place between two or more portions of the port body 464 in a fluid tight manner.

The port 464 can be accessed, with a male luer device that is inserted through the slit of the first valve 471. The male luer device can be interlocked with the luer threads if the male luer device includes a luer lock. In this manner, a separate access device can be coupled to the catheter assembly 410 through the port 464 to establish fluid communication there through. Additionally, a syringe, needle, or other such device can be inserted through the slit of the first valve 471 to withdraw fluids there through. Using the first valve 471, medical personnel can access the inner space 467 of the catheter hub 412 without being exposed to the patient's blood.

A blood control second valve 473 including a blood control septum 474 having at least one slit may be arranged within the inner space 467 of catheter hub 412 to prevent the outflow of fluid during and following removal of the needle 420. The second valve 473 can be configured with a plug 475 which is also housed in the inner space 467 of the catheter hub 412. The blood control second valve 473 can be elastomeric and designed to closely conform to the shape of a needle 420 to prevent leaking. The blood control second valve 473 can also seal upon removal of the needle 420 due to axial compression forces on the second valve 473 that induces the second valve to close. The second valve 473 can have an outer diameter that is configured to compatibly seat within a groove or channel or other suitable projections formed on an inner surface 456 of the catheter hub 412. Alternatively, a valve receiving means such as a groove or channel or other suitable projections can be formed on the outer surface 458-1 of the second valve 473, which interlocks with one or more features on the inner surface 456 of the catheter hub 412.

The second valve 473 can be configured with a plug 475 which is also housed in the inner space 467 of the catheter hub 412. The plug 475 is in fluid communication with the second valve 473 and inner space 467 of the catheter hub 412. The inner surface at a distal end 422-1 of the second valve 473 can be provided with at least one projection or groove or vice versa matching with said at least one projection or groove provided in an outer wall/surface 458-1 of the plug 475 at a proximal end 424-1 thereof. Accordingly, the inner surface at a distal end 422-1 of the second valve 473 can be provided with at least one projection matching with at least one groove provided in an outer wall/surface 458-1 of the plug 475 at a proximal end 424-1 thereof, or the inner surface at a distal end 422-1 of the second valve 473 can be provided with at least one groove matching with at least one projection provided in an outer wall/surface 458-1 of the plug 475 at a proximal end 424-1 thereof. The plug 475 may be made from a first material, e.g. a rigid plastic material or metal, and the second valve 473 may be made from a second material different from said first material for example, second material of the second valve 473 may be resilient, flexible material that is easily deformed when fluid is introduced to port via a syringe or other compatible device. Materials such as silicone, silicone rubber, or polyisoprene or the like can be used to form the second valve 473. The second valve 473 can be spaced from the first valve 471 being positioned within a fluid pathway through the inner space 467 of the hub 412 of the catheter assembly 410.

In some embodiments, the second valve 473 is tube or barrel shaped, while in other configurations, the second valve 473 is substantially cylindrical or disk shaped. The embodiments of the second valve 473 include other geometrical shapes and dimensions. The second valve 473 can be elastomeric and include one or more slits through which a septum activator can be inserted. The second valve 473 can include at least one slit. Alternatively, second valve 473 can include a plurality of slits. Slit can provide a fluid-tight seal, thereby preventing fluid from bypassing septum 474.

The proximal end 424 of the catheter hub 412 further comprises an opening 477 through which a separate secondary device may be inserted to infuse and withdraw fluid and/or liquid, such as a syringe or intravenous fluid line. In some instances, proximal end 424 comprises a set of threads configured to threadedly receive the secondary device in a secure manner. Opening 477 may further comprise a tapered opening to receive secondary device via an interference or friction fit. Proximal end 424 and opening 477 may alternatively comprise various surfaces and other features to enable coupling to a needle hub 416, a diagnostic device, and other suitable infusion therapy equipment.

As discussed above, upon deformation of the first valve 471 and second valve 473, fluid from the syringe or from the patient is permitted to bypass the deformed valve and flow into inner space 467 of the catheter hub 412. As the fluid pressure decreases, the resilient nature of the valve's 471, 473 material causes valves 471, 473 to restore their original shape, thereby once again blocking the fluid pathway. In some embodiments, valves 471, 473 may be secured within inner space 467 of the catheter hub 412 by any compatible means. For example, valves 471, 473 are secured within inner space 467 via an adhesive. In other embodiments, valves 471, 473 are secured within inner space 467 via an interference fit. Further, in some instances valves 471, 473 are inserted into an annular groove formed on the inner surface of the catheter hub 412. For example, the first valve 471 as shown in FIG. 3. is placed within inner space 467 so as to overlap and form a seal between inner space 467 and the pathway of the port 464. Both the first 471 and second 473 valves comprise a proximal opening, a distal opening, and a pathway extending therebetween. In some instances, proximal opening comprises a reduced diameter. The embodiment shown in FIG. 3 is without a needle guard 426. However, a needle guard 426 can be housed within the housing of catheter hub 412 and/or needle hub 416.

Figure 6A:
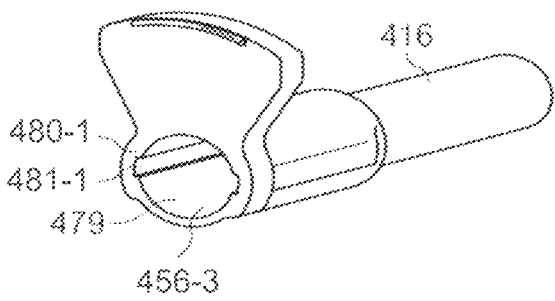
FIGS. 6A & 6B are perspective views of the needle hub of the intravenous catheter assembly according to one of the embodiments of the present invention.
Figure 6B:
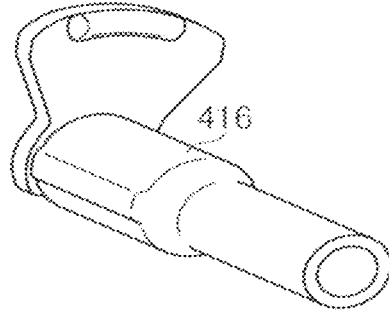

In another embodiment, as shown in FIG. 4A a needle guard 426 as shown in FIG. 4B is movably arranged on the needle shaft 428 and retained in a needle guard casing 478. The needle guard casing 478 can be movably retained in the needle hub 416 prior to use of the catheter assembly 410 as shown in FIGS. 4A, 4C & 4D. The needle hub 416 is provided with inner space 479 defining a housing to movably receive the needle guard casing 478 as shown in FIGS. 6A and 6B. The needle guard casing 478 has a substantially cylindrical shape, which is structurally beneficial to the provision of rotation capabilities.

Referring now to FIGS. 5A to 5D, the needle guard casing 478 comprises an upper part 482 and a lower part 483 together forming a chamber 476 for housing the needle guard 426. The upper part 482 of the needle guard casing 478 is received on the lower part 483. For example, the upper part 482 may be snap-fitted on the lower part 483. The snap-fit may be formed by a protrusion ring 484 and a corresponding groove ring 485 and which can be provided in both upper and lower part alternatively. The protrusion ring 484 may comprise the grooves and the groove ring 485 may comprise at least one projection or vice-versa. The ring of both the projections or groove can be a continuous ring or a spaced apart formation. Other ways and means for a secure engagement are also encompassed.

Both the upper part 482 and lower part 483 of the needle guard casing 478 can be provided with a chamber 476 to safely house the needle guard 426. In the upper part 482 the chamber 476 is provided in the bottom portion 487 whereas in the lower part 483 the chamber 476 is provided in the top portion 486. Both the upper part 482 and lower part 483 has a bore 488 to receive the needle 420. The inner diameter of the bore 488 has a close fit ratio with the outer diameter of the needle 420.

A distal end 422-2 of the upper part 482 can be provided with a fitment 489 which is received in the housing 448 of the catheter hub 412 creating a secure connection between the two. The fitment 489 also has a bore 488 which allows the needle 420 to pass there through. The inner diameter of the bore 488 has a close fit ratio with the outer diameter of the needle 420. When the needle guard casing 478 is secured completely within the needle hub 416 the fitment 489 remains exposed to be safely received in the housing 448 of the catheter hub 412. In other embodiments, for a safe and secure connection between the fitment 489 of the upper part 482 and the housing 448 of the catheter hub 412, an outer wall 458 of the catheter hub housing 448 is provided with at least one projection 480 or groove 481 or vice versa matching with said at least one projection 480 or groove 481 may be provided in an inner wall 456-2 adjoining said fitment 489. Thus, the needle guard casing 478 is safely secured with the catheter hub housing 448 by the means of change in dimensions. Alternative arrangements by way of replacing the change of dimensions within or outside the housing 448 and on the upper part 482 of the needle guard casing 478 can also be employed. For example, the upper part 482 of the needle guard casing 478 can be made without the fitment 489 and be snap-fitted with the catheter hub housing 448. The snap-fit may be formed by a protrusion ring 484 and a corresponding groove ring 485. The protrusion ring 484 may comprise the groove and the groove ring 485 may comprise at least one projection or vice versa. The ring of both the projections or groove can be a continuous ring or a spaced apart formation. Other ways and means for a secure engagement are also encompassed, for example as shown in FIGS. 4A, 4C & 4D. Further, there is a close fit ratio between the inner diameter of the bore 488 provided in the upper 482 and lower part 483 of the needle guard casing 478 and outer diameter of the needle 420.

As shown in FIGS. 6A and 6B, in order to enable the needle guard casing 478 to fit within the housing 479 of the needle hub 416, an inner wall 455-3 of the needle hub housing 479 can be provided with at least one projection 480-1 and/or groove 481-1 or vice versa matching with said at least one projection 480-1 and/or groove 481-1 is provided in an outer wall 458-3 of an upper 482 and/or lower 483 part of the needle guard casing 478. Thus, the needle guard casing 478 is safely secured within the needle hub housing 479 by the means of change in dimensions. Alternative arrangements by way of replacing the change of dimensions within the housing 479 and on the upper 482 and lower 483 part of the needle guard casing 478 can also be employed.

Figure 7A:
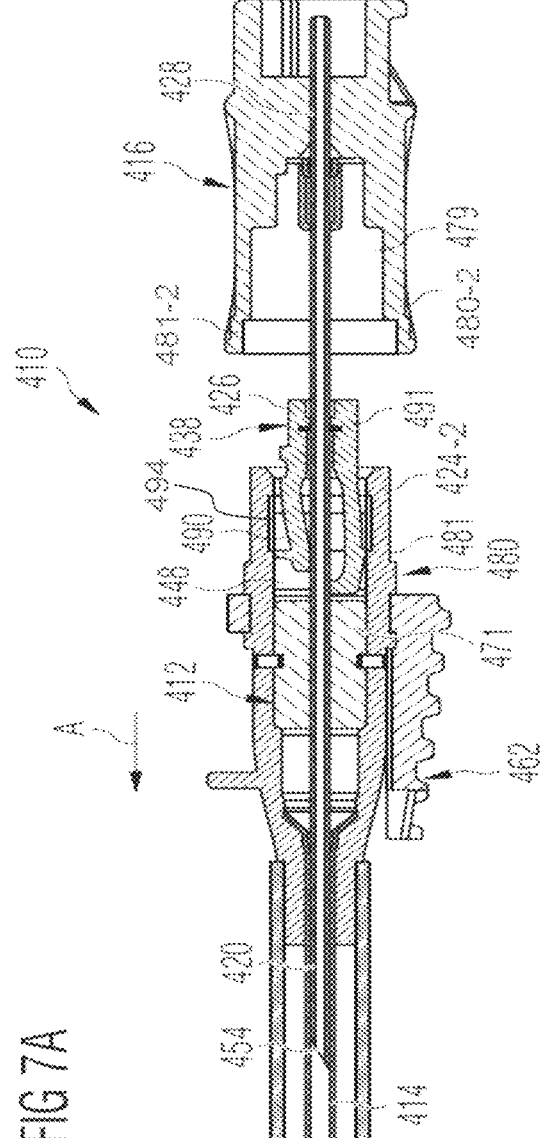
FIGS. 7A & 7B are a cross-sectional side views of the intravenous catheter assembly showing a catheter hub, a needle hub and a needle guard retained in the needle hub and catheter hub according to one of the embodiments of the present invention.
Figure 7B:
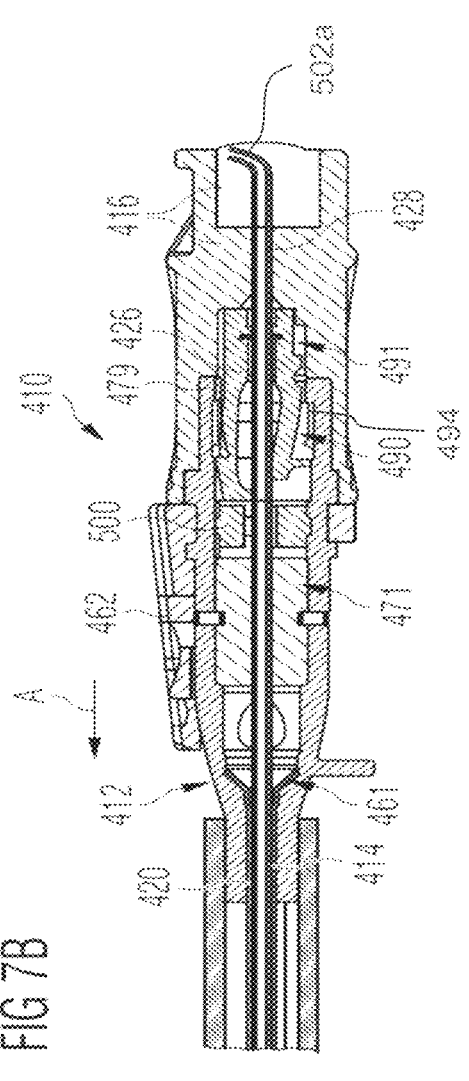

In another embodiment, as shown in FIGS. 7A & 7B the intravenous catheter assembly 410 of the invention can comprise a catheter hub 412 arranged at a proximal end 424-2 of a catheter tube 414 and defining a housing 448; a needle 420 defining an axial direction A and having a needle tip 454, wherein the needle 420 extends through the housing 448 and the catheter tube 414 when in a ready position; a needle guard 426 slidably arranged on the needle 420 and partly received in the housing 448 of the catheter hub 412 when the needle is in its ready position.

As shown, the needle guard 426 is movably arranged on the needle shaft 428 and an upper end 490 of the needle guard 426 is securely retained in the housing 448 of the catheter hub 412 exposing the lower end 491 of the needle guard 426. In the ready to use position, the entire catheter hub 412 portion with the lower end 491 of the needle guard 426 is securely retained in an inner space 479 of the needle hub 416. The needle hub 416 is provided with inner space 479 defining a housing to movably receive the catheter hub 412 and the lower end 491 of the needle guard 426. The housing 479 of the needle hub 416 has a substantially cylindrical shape, which is structurally beneficial to the provision of rotation capabilities.

In order to enable the catheter hub 412 to securely fit within the housing 479 of the needle hub 416, an inner wall 456-3 of the needle hub 416 housing 479 is provided with at least one projection 480-2 and/or groove 481-2 or vice versa matching with said at least one projection 480-2 and/or groove 481-2 is provided in an outer wall 458-2 of the catheter hub 412. Thus, the catheter hub 412 is safely secured within the needle hub 416 housing 479 by the means of change in dimensions. Alternative arrangements by way of replacing the change of dimensions within the housing 479 and outer wall 458-2 of catheter hub 412 can also be employed.

For example, the catheter hub 412 can be snap-fitted in the housing 479 of the needle hub 416. The snap-fit may be formed by a protrusion ring 484 and a corresponding groove ring 485. The protrusion ring 484 may comprise at least one groove and the groove ring 485 may comprise at least one projection or vice versa. The ring of both the projections or groove can be a continuous ring or a spaced apart formation. Other ways and means for a secure engagement are also encompassed.

As shown in FIG. 4B, the needle guard 426 can include a base portion 444 and first 440 and second 442 arms extending from the base portion 444, wherein the first arm 440 is deflected radially outwards by the needle 420 against a restoring force when the needle 420 is in its ready position whereby the needle guard 426 is brought into retaining contact with the catheter hub 412 by retaining means for retaining the needle guard 426 in the catheter housing 448 as long as the first arm 440 is in its deflected state. The base portion 444 has an axial through-bore 499 for receiving the needle 420. The inner diameter of the bore 499 has a close fit ratio with the outer diameter of the needle 420. The retaining means include a first disc-like retaining protrusion 493 provided on the first arm 440 and a retaining depression 494 formed in the inner surface 456 of the catheter hub 412 and adapted to receive the retaining protrusion 493.

The disc-like retaining protrusion 493 has the benefit that in the ready position it is in engagement along a circular contact surface with the corresponding retaining depression 494 formed in the inner surface 456 of the catheter hub 412. This provides an engagement between the needle guard 426 and the catheter hub 412 along a substantial annular portion of the retaining protrusion 493 and the retaining depression 494 which provides a safe and reliable engagement between the two components as long as the needle guard 426 is in its ready position and is to be prevented from being retracted out of the needle hub 416. Even if the needle guard 426 is rotated within the catheter hub 412, this secure engagement between the catheter hub 412 and the needle guard 426 holds the needle guard 426 safely within the catheter hub 412.

Because of a depression 494 being formed in the inner surface 456 of the catheter hub 412 for retaining the needle guard 426 in particularly the upper end 490 of the needle guard 426 in the housing 448, instead of e.g. a protrusion, the catheter hub 412 can be manufactured more easily and, thus, at less manufacturing cost, in particular if the catheter hub 412 is a plastic part and e.g. formed by injection molding. At the same time the particular design of the first retaining protrusion 493 provided on the needle guard 426 ensures effective engagement of the retaining protrusion 493 with the retaining depression 494 and, thus, reliable retaining of the needle guard 426 in the catheter hub 412. Hence, the risk of premature release of the needle guard 426 from the catheter hub 412 during withdrawal of the needle 420 from the catheter hub 412 and, thus, the risk of accidental pricking by the needle 420 is reduced.

In one embodiment, the retaining protrusion 493 can be of part-circular, in particular semi-circular shape. More specifically, the retaining protrusion 493 may have generally parallel proximal and distal faces and/or a convex, in particular part-cylindrical, peripheral surface.

According to another embodiment, the first retaining protrusion 493 can be arranged in the region of a distal end 422-3 of the first arm 440. According to yet another embodiment, a second disk-like retaining protrusion 495 is arranged on the second arm 442 and adapted to engage with the retaining depression 494 as long as the first arm 440 is in its deflected state. According to yet another embodiment, the second arm 442 can be deflected along its entire length radially inwards when the needle tip 454 is received between the arms 440, 442, to thereby allow the second retaining protrusion 495 to disengage from the retaining depression 494.

According to yet another embodiment, the second retaining protrusion 495 can be arranged in the region of a distal end 422-4 of the second arm 442. In particular, the second retaining protrusion 495 may be arranged opposite from the first retaining protrusion 493. According to yet another embodiment, the retaining depression 494 is an at least part-annular depression, preferably an annular depression.

To explain further, the first arm 440 of the needle guard 426 can be longer than the second arm 442 and has a massive distal wall 418 having an undercut for catching the needle tip 454. The distal wall 418 is arranged at a distal end 422-3 of the first arm 440 and extends in a direction transverse to an axial direction A of the needle 420 such that the distal wall 418 completely blocks the needle 420. The distal wall 418 ensures that the needle tip 454 is prevented from axially projecting out or sideways projecting out of the needle guard 426. The distal wall 418 has a bigger dimension than the distal surface of the second arm 442 and much bigger dimension than the outer diameter of the needle 420 such that the distal wall 418 completely covers and blocks the needle tip 454 once confined and entrapped within the needle guard 426. The first and second arms 440, 442 of the needle guard 426 extend generally in the axial direction A from a distal side 460 of the base portion 444, i.e. generally parallel to the needle shaft 428.

In the ready position, the first arm 440 deflects outward of the needle guard 426 such that the distal wall 418 of the first arm 440 is supported on the needle shaft 428. Further, in this ready position, the first and second arms 440, 442 do not engage or interact with an inner wall/surface 456-4 of the housing 448 prior and during venipuncture of a patient. This non-contact of the first and second arms 440, 442 with the inner surface 456-4 of the housing 448 significantly decreases the withdrawal force required and friction caused when a needle 420 is withdrawn through a catheter hub 412 being protected by a needle guard 426 after use.

Upon withdrawal of the needle 420 from the catheter tube 414 and catheter hub 412 the needle shaft 428 moves relative to the needle guard 426 while the needle guard 426 is retained in the catheter hub 412 until the needle tip 454 is received in the needle guard 426. Once the needle tip is received in the needle guard 426 the enlargement 496 of the needle shaft 428 engages with the base portion 444 of the needle guard 426 via a stopping element 438 such that the needle guard 426 can be pulled out of the catheter hub 412 together with the needle 420. An axial movement of the needle 420 relative to the needle guard 426 is now limited, as the distal wall 418 blocks the needle tip 454 axially and the engagement between the enlargement 496 and the base portion 444 via the stopping element 438 prevents the needle tip 454 from being removed via the base portion 444, i.e. the needle tip 454 is safely surrounded by the needle guard 426.

The needle 420 can comprise an engagement means provided at a distance from the needle tip 454 for engaging with the needle guard 426 and preventing the needle guard 426 from sliding off the needle 420. Preferably, the engagement means is formed of by enlargement 496 of the radial dimension of the needle 420 in at least one direction as compared with a principal profile of the needle 420. The engagement means can be found by a local crimp, a shoulder, a bulge formed as an annular widening etc.

As mentioned above, the needle guard 426 can comprise a stopping element 438 engaging with the engagement means of the needle 420 when the needle tip 454 is received between the first 440 and second 442 arms. Preferably, the stopping element 438 defines an axial bore having a cross-section adapted to the principal profile of the needle 420 but being smaller than the enlargement 496 of the needle 420. Furthermore, the stopping element 438 may be made of a material different from the material of the base portion 444, in particular of a metal material. The stopping element 438 may be of disc-like shape or tubular shape and/or arranged on a distal side 460 of the base portion 444. It can be fixed in the base portion 444 or supported in a floating manner on the needle 420.

The catheter assembly 410 is particularly inexpensive to manufacture if the base portion 444, the first and second arms 440, 442 of the needle guard 426 are integrally made from a first material. The first material may, for example, be a plastic material. Thus, the base portion 444, the first and second arms 440, 442 could be manufactured by injection molding.

Alternatively, the base portion 444, and one of the first and second arms 440, 442 can be integrally made from a first material, e.g. a plastic material, and the other one of the first and second arms 440, 442 can be made from a second material different from said first material. For example, said other one of the first and second arms 440, 442 can include a strip of material having spring-like properties, e.g. a strip of sheet metal, providing the above-mentioned inherent elasticity.

The restoring force is created by at least one of an elastic property of the first arm 440 and an additional tension element 446. The tension element 446, for example, a rubber band or the like, surrounds the first and second arms 440, 442. The tension element 446 at least partly surrounding the arms 440, 442 in a region proximal of the first retaining protrusion 493 or—instead of surrounding the two arms 440, 442—biasing the two arms 440, 442 by a linear biasing action. Alternatively or additionally, the first 440 and second 442 arms can be made of a resilient material having elastic properties.

The construction and shape of the improved intravenous catheter assembly 410 according to the various embodiments of the present disclosure provides a simple configuration. The simple and compact design of the intravenous catheter assembly 410 according to the above disclosure is advantageous in a clinical setting because it smoothens the whole catheterization process thereby reducing injury or discomfort to a patient and provides better blood control features. In addition, such design greatly reduces manufacturing costs and is efficient, effective and simple in its construction and use.

In the following embodiments, reference will only be made to the specific new features described therein. The remaining features of the catheter assembly may be the same as for those in the embodiments described above and the following describes features may be combined with any of the catheter assemblies or other features described herein.

Figures 8A, 8B, 8C, 8D, 8E:
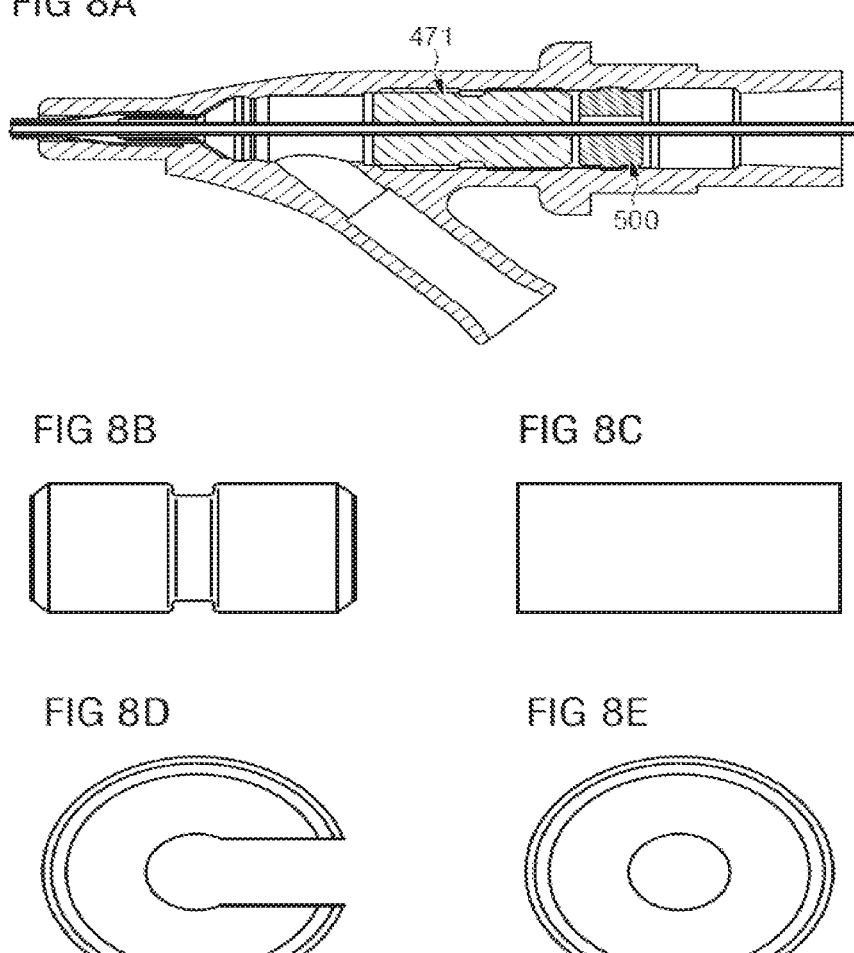
FIGS. 8A-8E are views of a disc and second valve that can be used in combination with any of the catheter assemblies described in the present invention.

As shown in FIG. 8A, the catheter assembly may include a disc 500 arranged proximate to the first valve 471, the second valve 473, or both the first and the second valve. In the embodiment shown in FIG. 8A, the disc 500 is arranged proximate to the first valve 471. As described above, the first valve 471 or the second valve 473 can be elastomeric and be designed to closely conform to the shape of a needle 420 to prevent leaking. The valve can have any geometrical shape and dimension. In a preferred embodiment, the valve can have a dumbbell form as shown in FIG. 8B. In a further preferred embodiment, the valve can have a tube or barrel form as shown in FIG. 8C. The tube or barrel form can have the advantage that is easy and cheap to be manufactured. While reference is made to the first valve 471 in the above discussion, the disc 500 may also be arranged proximate to the first valve 473, wherein the same considerations regarding the shape and dimensions apply.

The disc 500 may be arranged in direct contact or close to (i.e. spaced apart from) any of the valves 471, 473. The disc 500 may be arranged proximal or distal to the valve. The disc 500 may have circular or part-circular profile, a profile of a C-shape as shown in FIG. 8D, a ring-shape (or closed circle, full round shape) as shown in FIG. 8E. or any other shape such as a half-circle (not shown). The disc 500 can be configured to hold the valve in its position, for instance due to interaction of the disc 500 with alignment features in the inner wall of the catheter hub. The alignment features may be a recess or groove formed in the interior surface of the catheter hub, while the disc 500 comprises a corresponding projection or protrusion configured to engage the recess or groove, as may be seen in FIG. 8A. The disc 500 can be configured such that at a high pressure, the valve arranged proximate to the disc 500 does not displace from its position.

Figure 9A:
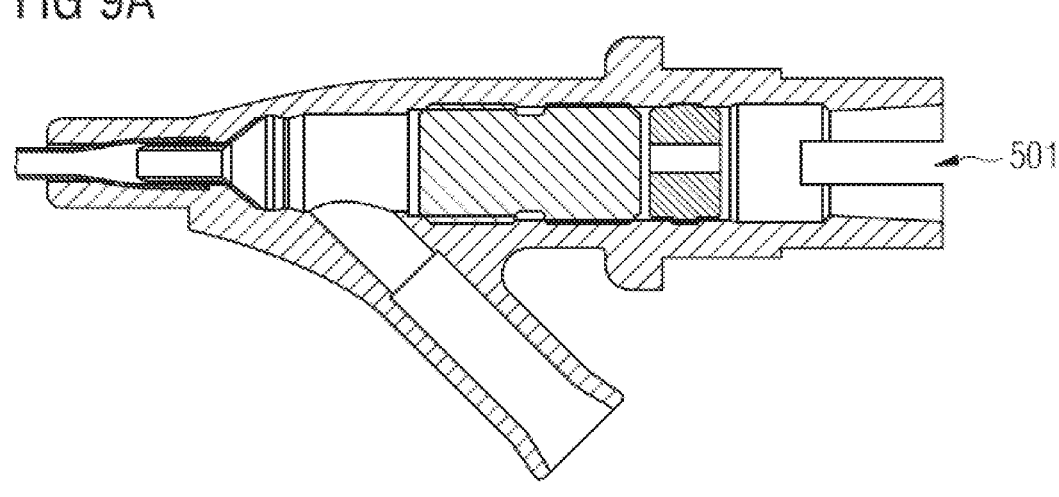
FIGS. 9A and 9B are views of a cut at the proximal end of a catheter hub that can be used in combination with any of the catheter assemblies described in the present invention.
Figure 9B:
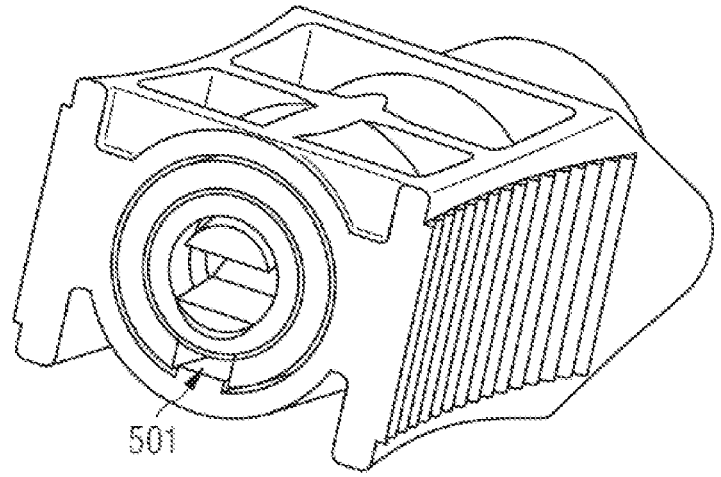

As shown in FIGS. 9A and 9B, the proximal end of the catheter hub may include at least one cut 501. The catheter hub 412 may include two cuts 501 on opposite sides of the proximal end of the catheter hub. The at least one cut 501 may be formed by cutting a slit into the proximal end of the catheter hub or by molding the catheter hub to include the cut or slit at a proximal end of the catheter hub. The cut 501 may have a rectangular shape as shown in FIG. 9A or any other shape, such as a slit shape or V shape. The cut 501 may support locking of the catheter hub 412 with the needle hub 416. The cut 501 may further restrict the rotation of the catheter hub 412 with respect to the needle hub 416, for instance be interacting with corresponding protrusion on the needle hub 416. The cut 501 may also be configured to reduce the withdrawal force required to withdraw the needle hub 416 from the catheter hub 412. The reduction of the withdrawal force may be provided, as the flexibility of the proximal end 424 of the catheter hub is increased by the cut 501.

Figure 10A:
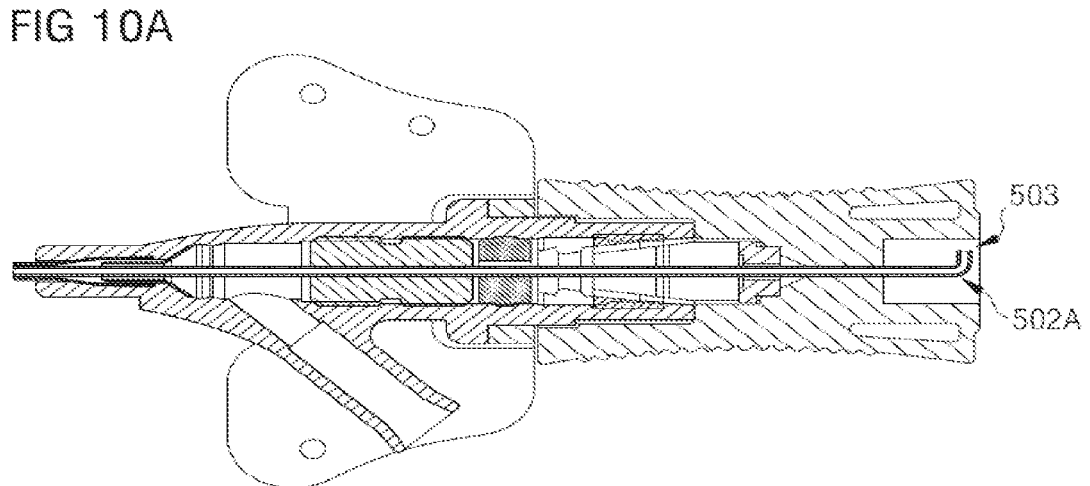
FIGS. 10A, 10B and 10C are views of proximal needle feature that can be used in combination with any of the catheter assemblies described in the present invention.
Figure 10B:
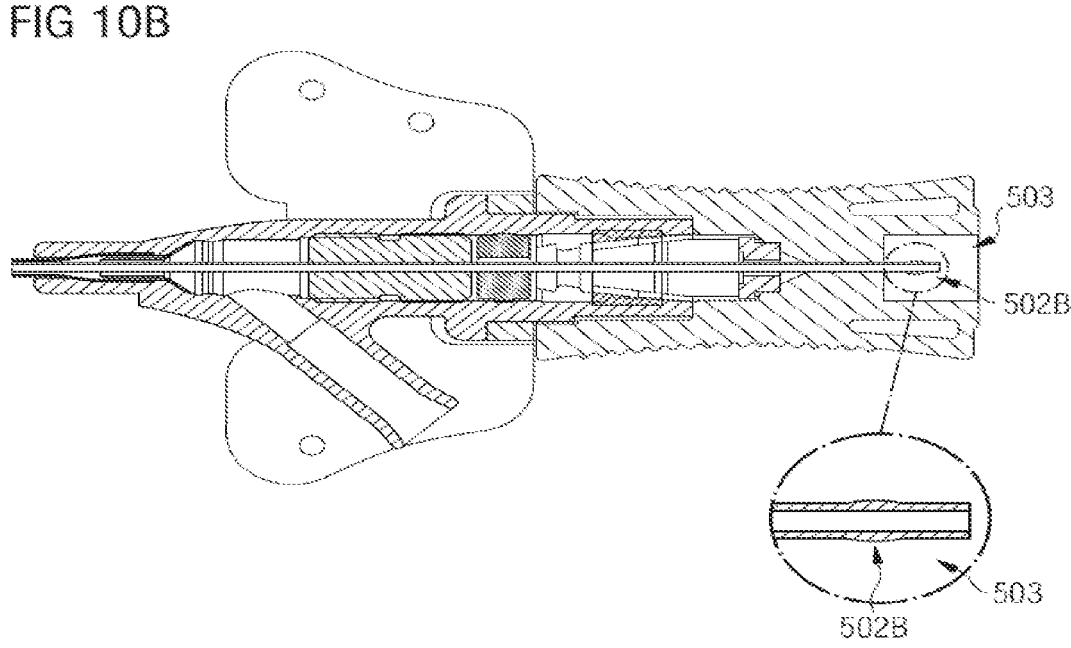
Figure 10C:
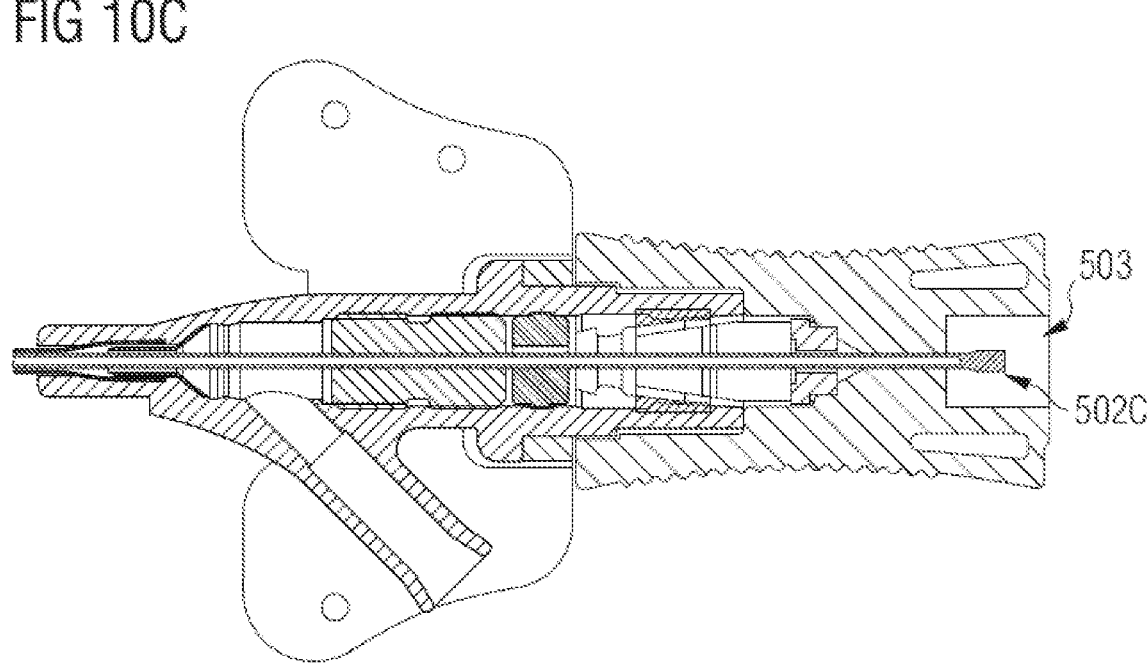

As shown in FIGS. 10A, 10B and 10C, the needle 420 may comprise a proximal needle feature 502 at the proximal end, opposite to the needle tip end. The proximal needle feature 502 comprises a deformation that may be a needle bend 502A as shown in FIG. 10A, a needle crimp 502B as shown in FIG. 10B or a needle pressing 502C as shown in FIG. 10C. In case of a needle bend 502A, the needle may comprise only a slight needle bend or a complete needle bend. In case of a needle crimp 502B, the needle may be crimped at the proximal end with any known method known to the skilled person. In case of a needle pressing 502C, the needle may be pressed at its proximal end. The proximal needle feature 502 may be located at a proximal end of the needle hub 416 as shown in FIGS. 10A, 10B and 10C. The proximal needle feature 502 may be attached to the proximal end of the needle hub 416 by a needle fixation means 503 such as glue. The needle fixation means 503 such as the glue may also seal the proximal needle end. The proximal needle feature 502 can, in addition to the needle fixation means 503, increase the force required to separate the needle 420 from the needle hub 416. In one embodiment, the needle is assembled with the needle hub and then crimped, bend or pressed.

As shown in FIGS. 11A, 11B, 11C and 11D, and as already described further above, the catheter hub 412 may be provided with wings 462 which in use may be adhesively taped to the skin of the patient at the venipuncture site to maintain the catheter assembly/device 410 stationery during the infusion. While the wings 462 may be integrally formed with the catheter hub, as shown in FIG. 1, the following describes separate wings 462 that may be affixed to the catheter hub.

Figure 11A:
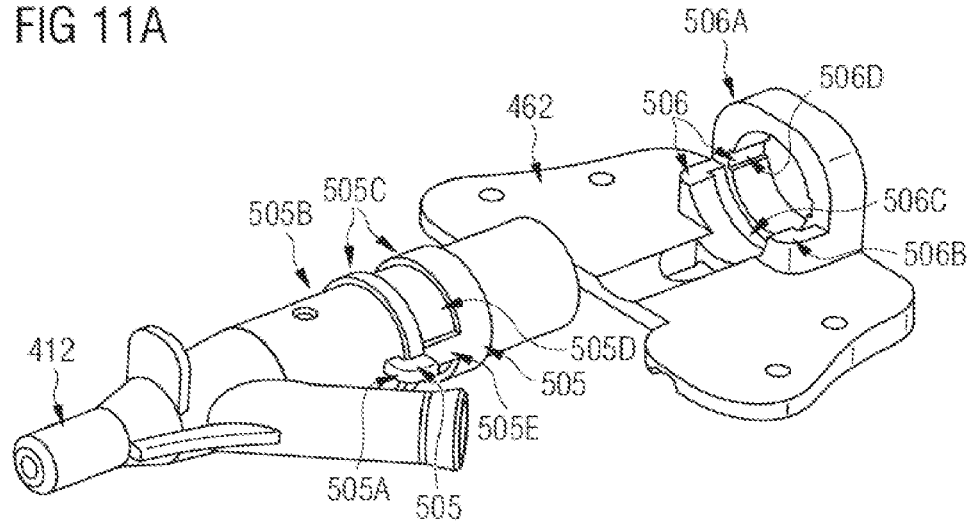
FIGS. 11A, 11B, 11C and 11D are views a wing alignment feature and a catheter hub alignment feature that can be used in combination with any of the catheter assemblies described in the present invention.
Figure 11B:
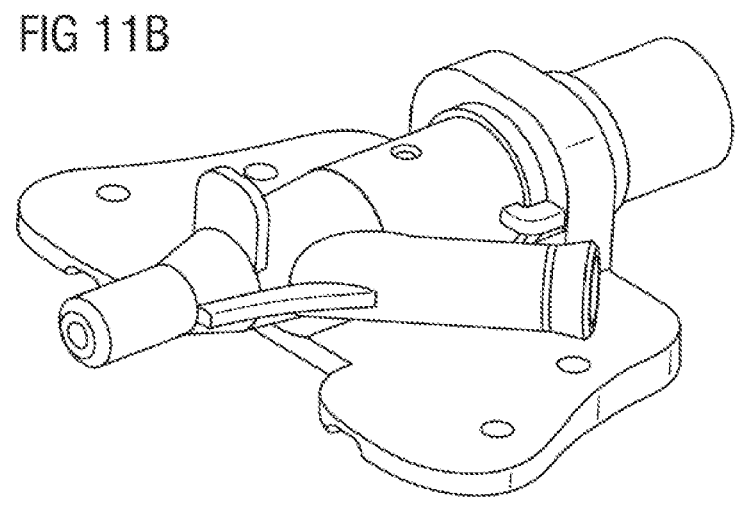
Figure 11C:
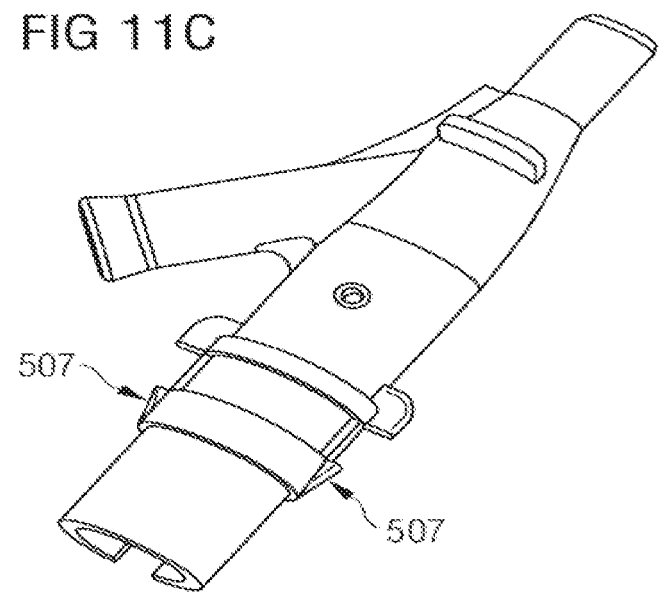
Figure 11D:
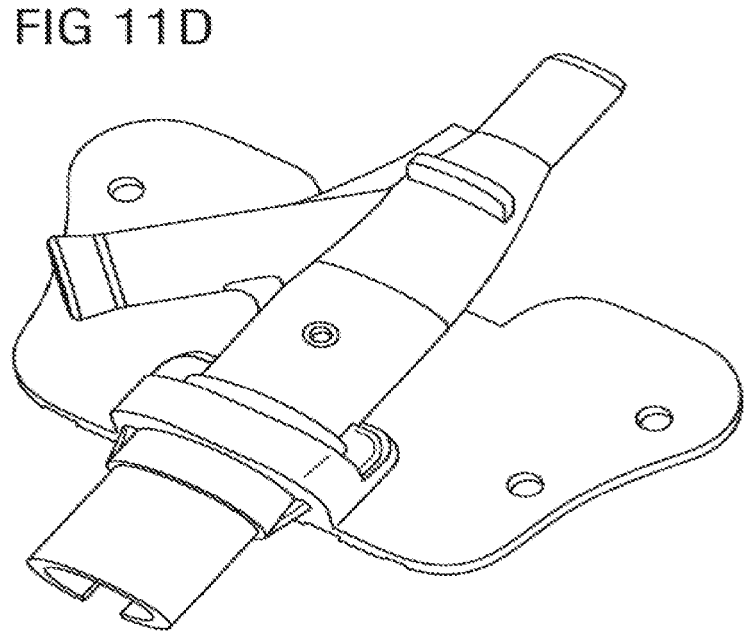

As shown in FIGS. 11A and 11B, the catheter hub 412 may include at least one wing alignment feature 505 that is configured to interact with at least one catheter hub alignment feature 506 on the wings 462. The wing alignment feature 505 can be configured to restrict or prevent wing rotation. The wing alignment feature 505 can comprise at least one wing alignment projection 505A extending from the outer surface of the catheter hub 412. The wing alignment feature 505 may comprise at least one wing alignment projection 505A. In the embodiment shown in FIG. 11A, the wing alignment feature 505 comprises two wing alignment projections 505A extending in opposite radial direction from the outer surface of the catheter hub 412 as can be seen in FIG. 11C, The at least one wing alignment projection 505A may be arranged in the same plane as the wing members 510, i.e. the wing members 510 extend in a first plane, e.g. a horizontal plane, and the wing alignment projection or projections 505A extend in the same plane. The at least one wing alignment projection 505A may be configured to prevent distal movement of the wings 462 as well as to prevent wing rotation. The wing alignment projection 505A may be in the form of a rib, a nose-like or a ramp-like shape, with its radial dimension increasing in proximal direction. A proximal face of the wing alignment projection 505A can extend in a plane generally perpendicular to the axial direction, i.e. in a radial plane. The proximal face of the wing alignment projection 505A can be configured to interact with a corresponding element of the wings 462 to prevent distal movement of the wings 462 beyond the wing alignment projection 505A. Side faces of the wing alignment projection 505A extend in a plane generally parallel to the axial direction. At least one of the side faces of the wing alignment projection 505A can be configured to interact with a corresponding element of the wings 462 to prevent rotational movement of the wings 462 beyond the wing alignment projection 505A. The wing alignment projection 505A may be integrally formed with the catheter hub 412.

The wing alignment feature 505 may further comprise a wing alignment element 505B. The wing alignment element 505B may include at least one annular projection 505C extending outwardly from the outer surface of the catheter hub 412. In one embodiment, the wing alignment element 505B may include two annular projections 505C spaced apart from each other in axial direction A, thereby forming a annular recess 505D between the two annular projections. The annular recess 505D may have the same outer diameter as the outer diameter of the catheter hub, while the two annular projections 505C have a greater diameter than the outer diameter of the catheter hub. The wing alignment element 505B may further include at least one lateral projection 505E formed on the annular recess 505D and connecting the two annular projections 505C in axial direction A. The wing alignment element 505B, including the annular projections 505C, the annular recess 505D and the lateral projection 505E may be integrally formed with the catheter hub 412.

The wing alignment element 505B may only comprise one annular projection 505C provided such that an annular recess 505D, which may have the dimension of the catheter hub, is arranged distal to the annular projection 505C. This wing alignment element 505B may still comprise a lateral projection 505E extending distally from annular projection 505C.

The wing alignment feature 505 may also have no annular projections, but only include an annular recess 505D having a smaller diameter than the outer diameter of the catheter hub. In this embodiment, the lateral projection 505E has the same diameter as the outer diameter of the catheter hub.

Any of the above described wing alignment elements 505B can be configured to guide and orient the wings 462 during assembly of the wings with the catheter hub 412. The wing alignment element 505B may further be configured to prevent wing rotation. The at least one wing alignment projection 505A may be provided on any of the annular projections 505C, preferably on the distal annular projection 505C.

In one embodiment, the wings 462 may comprise a catheter hub alignment feature 506 configured to align and orient with the catheter hub 412. The catheter hub alignment feature 506 may comprise a wing base 506A. The wing base 506A may have a tubular or ring-like body, at a bottom part of which the two wing members 510 extend from. The wing members 510 can either be formed integrally with the wing base 506A, or they can be separate elements that are attached to the wing base. The wing base 506A can be configured to receive the proximal end of the catheter hub. The wing base 506A can further be dimensioned to allow passage of the catheter hub, but to interact with or block the wing alignment projection 505A to prevent distal movement of the wings 462 beyond the wing alignment projection 505A.

The catheter hub alignment feature 506 may further comprise a wing socket 506B. The wing socket 506B may have a semi-circular or half-ring shape and may be provided distal to the wing alignment projection 505A. The wing socket 506B can be configured to interact with the wing alignment projection 505A to prevent wing rotation. Specifically, the wing socket 506B can comprise a top surface that interacts with a side face of the wing alignment projection 505A. The side face of the wing alignment projection 505A can be configured to interact with the top surface of the wing socket 506B to prevent rotational movement of the wings 462 beyond the wing alignment projection 505A. The wing socket 506B can be integrally molded with the wing base 506A, i.e. the wing socket 506B can extend in distal direction from wing base 506A.

A slot 506C may be provided between the wing base 506A and the wing socket 506B. The slot 506C can be configured to receive one of the annular projections 505C of the catheter hub.

The wing base 506A may comprise an indent 506D, for example in the form of a groove or other recess configured to receive the lateral projection 505E.

The wing alignment feature 505 may further comprise at least one stopper element 507. The stopper element 507 can have generally nose-like or ramp-like shape, with its radial dimension increasing in distal direction. A distal face of the stopper element 507 extends in a plane generally perpendicular to the axial direction, i.e. in a radial plane. The stopper element 507 may be provided on the proximal annular projection 505C. At least two stopper elements may be provided on opposite sides of the catheter hub. The stopper element 507 may be made of a resilient material. The stopper element 507 may be configured to deflect to let the wing base 506A pass in distal direction. The stopper element 507 may further be configured to take its original undeflected state after the wing base 506A has passed, thereby locking the wings 462 between the stopper element 507 and the wing alignment projection 505A, as shown in FIG. 11C. The stopper element 507 can be resiliently deformed to allow. The position of the stopper element 507 can be on the same plane as the wing members 510 and the wing alignment projection 505A of the wings 462.

In one embodiment, the catheter assembly comprises a catheter hub 412 with a wing alignment feature 505 and wings 462 with a catheter hub alignment feature 506, wherein the wing alignment feature 505 and the catheter hub alignment feature 506 are configured to align and orient the catheter hub and the wings with each other. The wing alignment feature 505 of the catheter hub comprises two wing alignment projections 505A such as two ribs extending in opposite radial direction from the outer surface of the catheter hub 412. The wings 462 comprise a tubular shaped wing base 506A, the distal side of which interacts with the wing alignment projections 505A to prevent distal movement of the wings beyond the catheter hub alignment feature 506. The wing alignment projections 505A further comprise a wing alignment element 505B comprising two annular projections 505C spaced apart and forming an annular recess 505D therebetween, wherein two lateral projections 505E connect the two annular projections 505C in axial direction A. The two wing alignment projections 505A are arranged on the distal one of the annular projections 505C and extend outwardly therefrom. Further, two stopper elements 507 are provided on the proximal one of the two annular projections 505C. The two wing alignment projections 505A, the two lateral projections 505E and the two stopper elements 507 are each provided on the same plane as the plane of the wing members 510 and on opposite sides of the catheter hub 412. The wings 462 comprise a wing base 506A with two indents 506D aligned with and configured to receive the lateral projections 505E. The wings 462 further comprise a wing socket 506B with a slot having a dimension configured to receive the distal one of the annular projections 505C. The interaction of the wing alignment feature 505 and the catheter alignment feature 506 provides that the wings 462 are properly aligned and oriented with the catheter hub 412 and can be safely and easily assembled. Further, the interaction of the wing alignment feature 505 and the catheter hub alignment feature 506 provides that the wings 462 cannot move into distal or proximal direction and cannot rotate with respect to the catheter hub 412 after assembly.

Figure 12A:
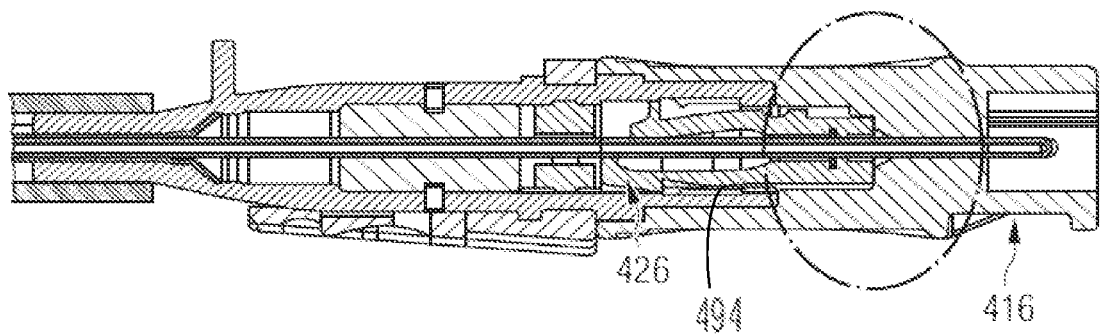
FIGS. 12A and 12B are views of a needle guard engaging element that can be used in combination with any of the catheter assemblies described in the present invention.
Figure 12B:
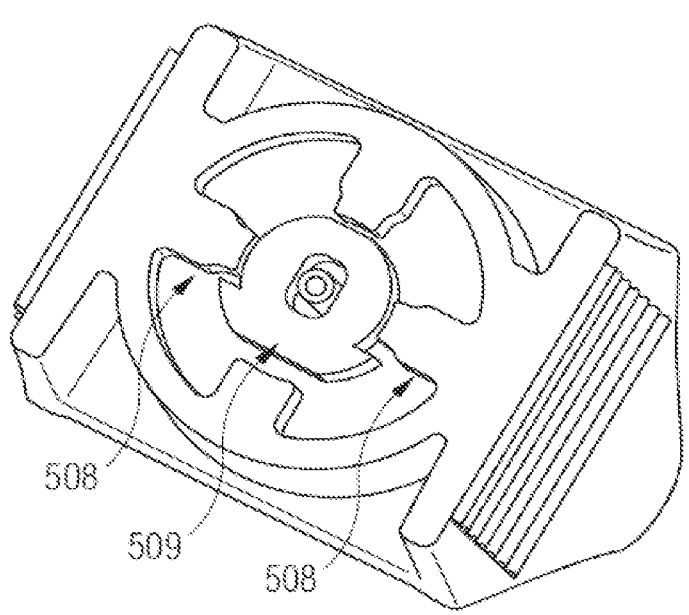

As shown in FIGS. 12A and 12B, the needle hub 416 may comprise at least one needle guard engaging element 508 configured to restrict the rotation of the needle guard 426. The at least one needle guard engaging element 508 may be a rib extending from the inner wall of the needle hub 416 or extending from the needle guard casing 478 towards the center. The at least one needle guard engaging element 508 may be arranged at a base of the needle hub 416 or needle guard casing 478. The at least one needle guard engaging element 508 may be positioned at the lower part 483 of the needle guard casing 478. The needle guard may comprise a corresponding needle guard anti-rotation element 509 configured to engage the needle guard engaging element 508.

Figure 13A:
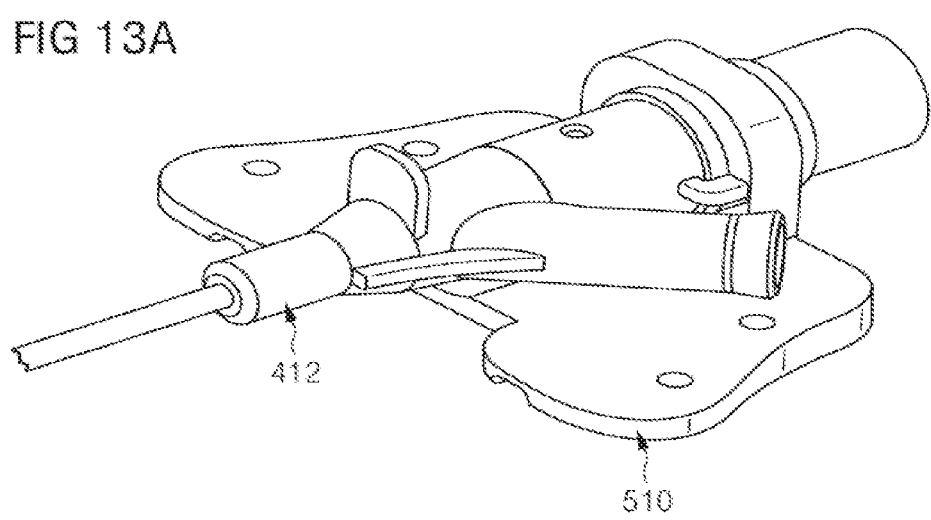
FIGS. 13A and 13B are views of the wing members that can be used in combination with any of the catheter assemblies described in the present invention.
Figure 13B:
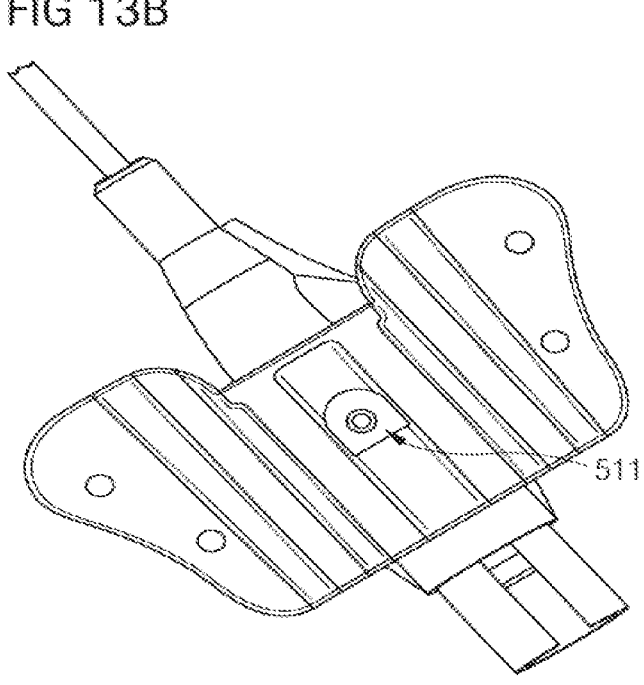

As shown in FIGS. 13A and 13B, the wings 462 may comprise two wing members 510. Each wing member may be made of a soft material, which may be selected from thermoplastic elastomers (TPE), polyvinylchloride (PVC), isoprene, rubber, ethylenevinylacetate (EVA), and other elastomeric or resilient materials. Each wing member may be made of a rigid material, for instance comprising polypropylene (PP). Each wing member may also be made of a combination of a soft and a rigid material selected from the above materials. Each wing member may comprise at least one through-hole as shown in FIGS. 13A and 13B. The wings 462 may further comprise a window 511 configured for air venting. The window 511 may be provided in the bottom part of the wing base 506A connecting the two wing members 510.

Figure 14A:
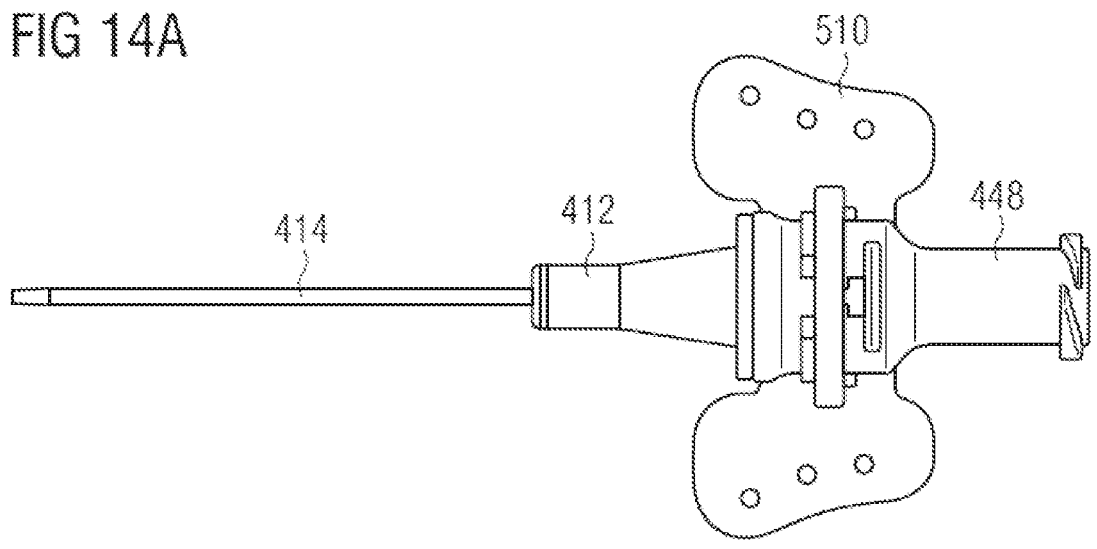
FIGS. 14A and 14B are views of a tapered profile of the wings that can be used in combination with any of the catheter assemblies described in the present invention.
Figure 14B:
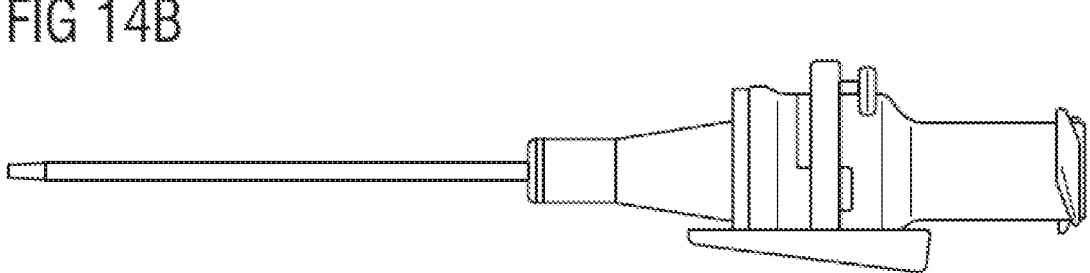

As shown in FIGS. 14A and 14B, the wings 462 may have a tapered profile. The tapered profile may have an increasing width in proximal direction. The taper may also have a nose-like or a ramp-like shape, with its radial dimension increasing in proximal direction. The tapered profile can support the alignment of the device with a patient's body and can support the insertion of the needle.

Figure 15:
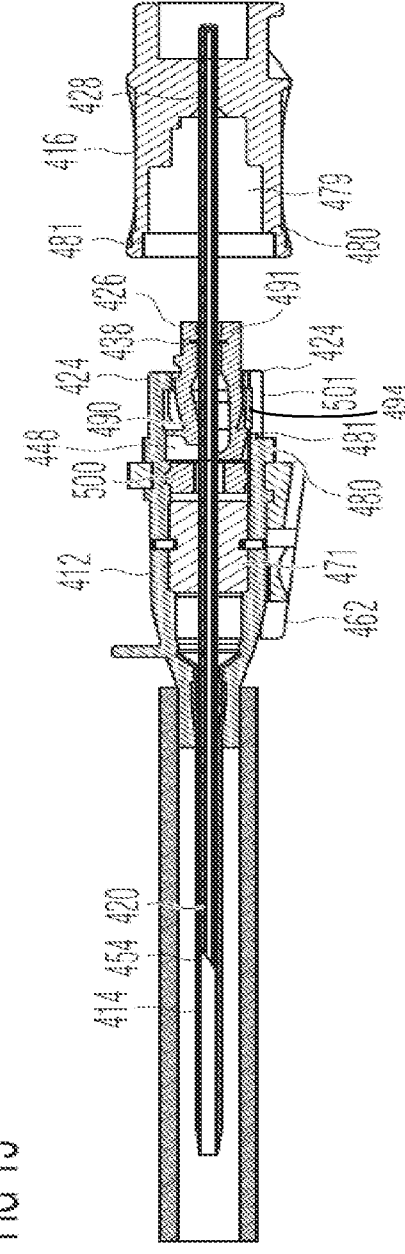
FIG. 15 is a view of a curved/tapered proximal end of the catheter hub that can be used in combination with any of the catheter assemblies described in the present invention.

As shown in FIG. 15, the proximal end 424 of the catheter hub 412 may be curved and/or tapered. The curved and/or tapered proximal end 424 may simplify assembly of the catheter hub 412 with the needle hub 416.

Figure 16A:
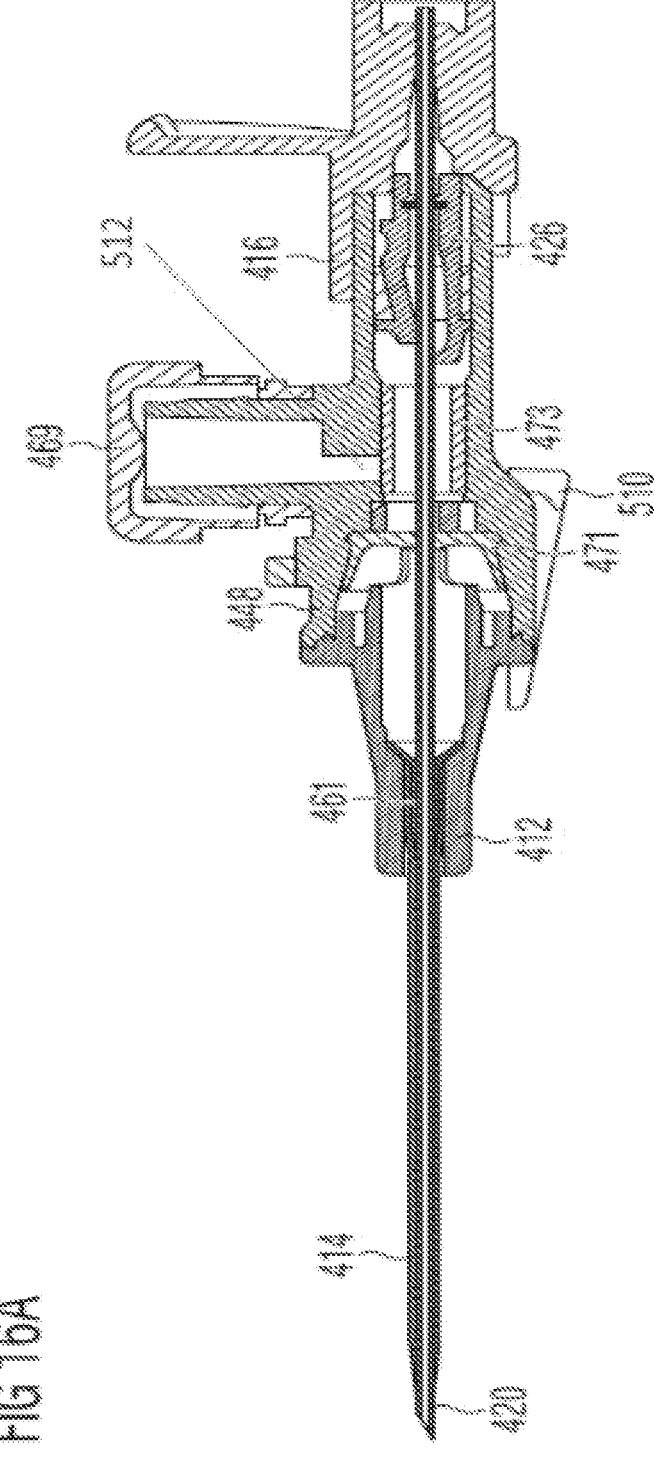
FIGS. 16A and 16B are views of a port hole of the port that can be used in combination with any of the catheter assemblies described in the present invention.
Figure 16B:
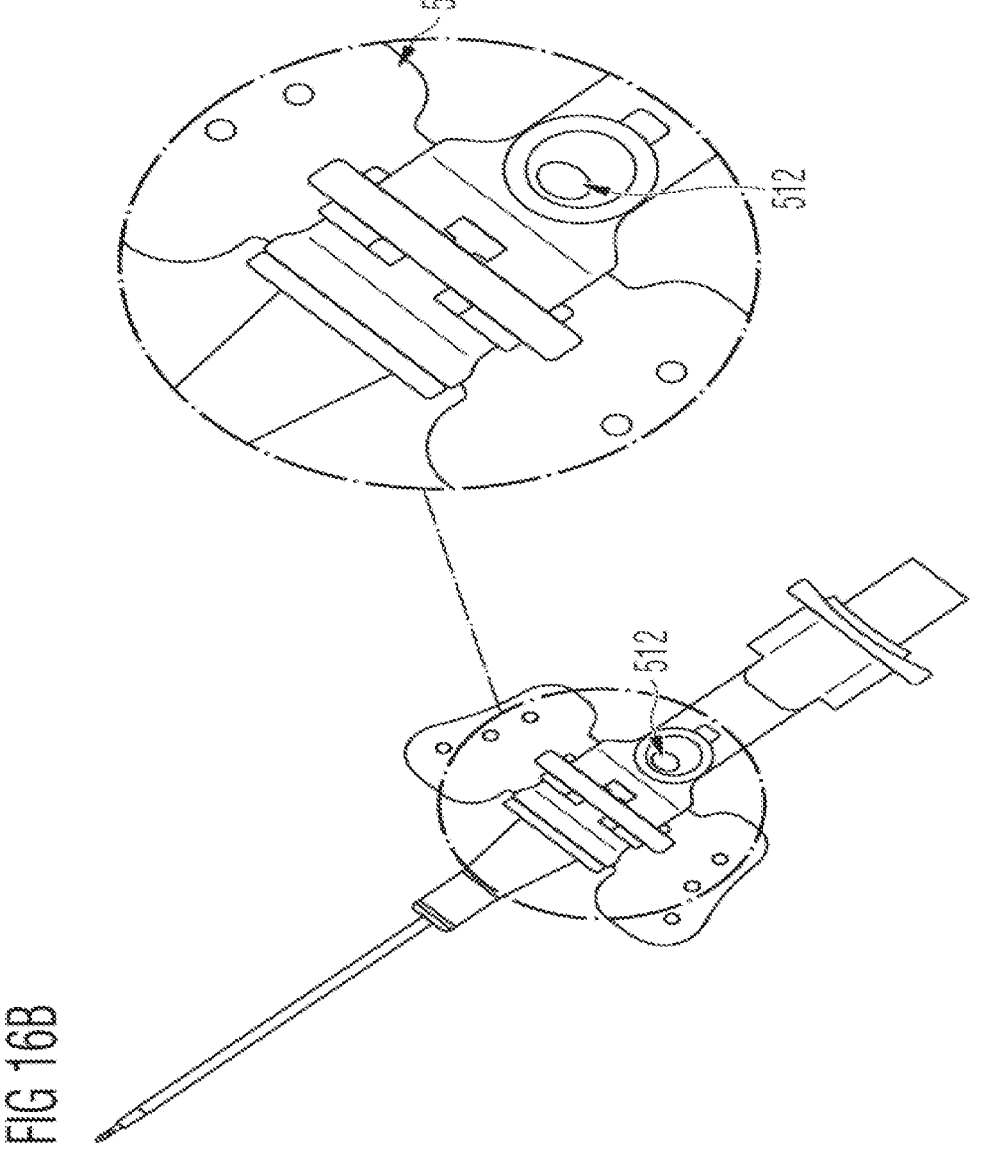

As shown in FIG. 16A, and as described in further detail above, the catheter assembly can comprise a port 464. The port 464 has an opening 465 defining an inlet and a bore 466 extending between the inlet and the opening 468 of the inner space 467 of the catheter hub 412. The port 464 is covered with a port cap 469. As shown in FIG. 16B, the port may include a port hole 512, The port hole 512 may be provided in the port 464. The port hole 512 can contribute in directional flow of fluid through the port 464. The port hole profile and location can be changed and the specific position and design of the port hole 512 can be configured to optimize the flow and pressure balance.

FIGS. 17A, 17B, 17C, 17D, 17E, and 17F show different configurations of a valve. The valve may be the first valve 471 or the second valve 473. Corresponding valves are described in further detail in WO 2014/153302, the contents of which are incorporated herein by reference.

The valve described in connection with any of the embodiments herein may comprise an elastomeric member 513 having a peripheral wall 514 projecting from a base surface 515. The base surface 515 can comprise at least one slit 516, which passes through the thickness of the base surface 515. The elastomeric member 513 can have a lateral annular protrusion 517 from edge of the base surface 515 configured to be received by a recess (not shown) within an interior wall of the catheter hub. The lateral annular protrusion 517 can support the holding of the valve in the catheter hub. The lateral annular protrusion 517 may not be required, for instance in cases in which a disc 500 is provided, as described in further detail above. In addition, the elastomeric member 513 can include a vertical annular projection 518 from the base surface 515 for providing interference with the catheter hub.

Figures 17A, 17B, 17C, 17D, 17E, 17F:
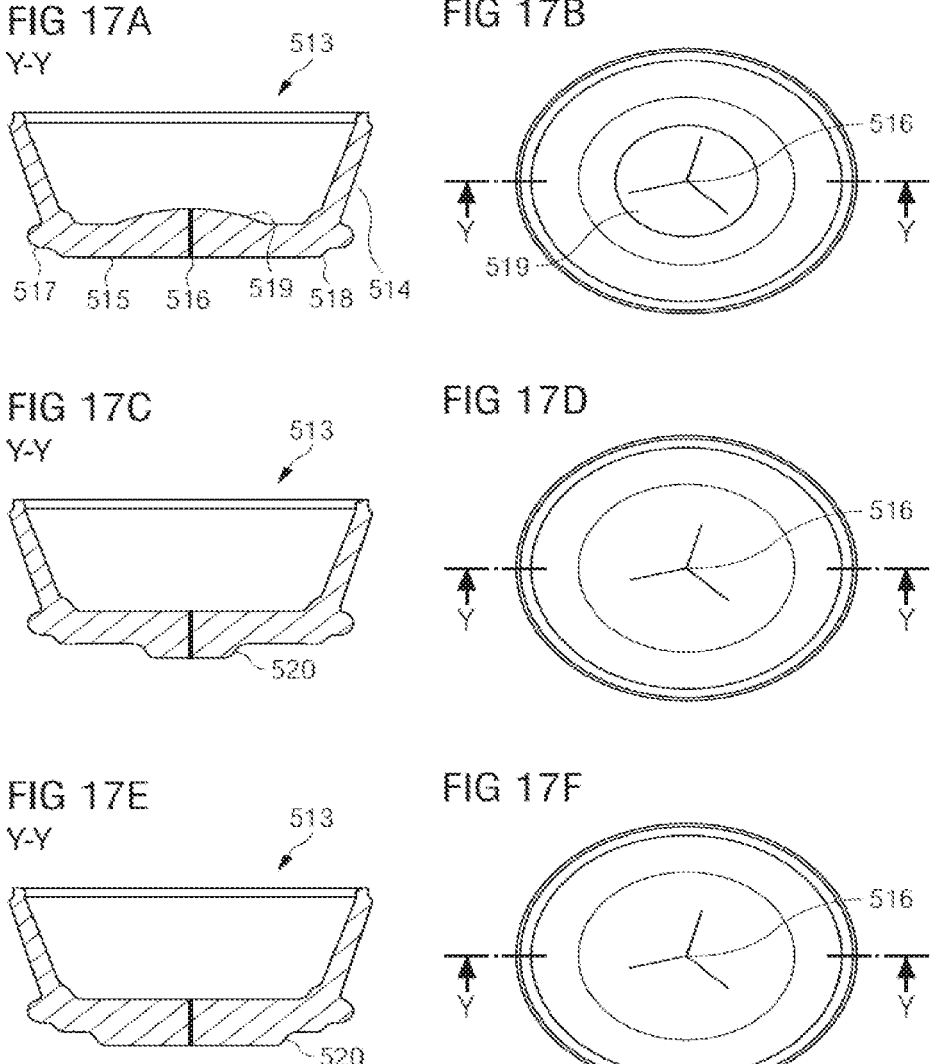

As shown in FIGS. 17A and 17B, the base surface 515 can include an inner vertical projection 519 extending from the base surface 515 in the direction of the peripheral wall 514. The inner vertical projection 519 may have a rounded shape, as shown in FIGS. 17A and 17B.

As shown in FIGS. 17C and 17D, the base surface 515 can include a second vertical projection 520 extending from the vertical annular projection 518. The second vertical projection 520 may have a smaller diameter than the vertical annular projection 518, as shown in FIGS. 17C and 17D. FIGS. 17E and 17F show a further configuration of the second vertical projection 520 with a larger diameter.

Figures 18A, 18B, 18C, 18D, 18E:
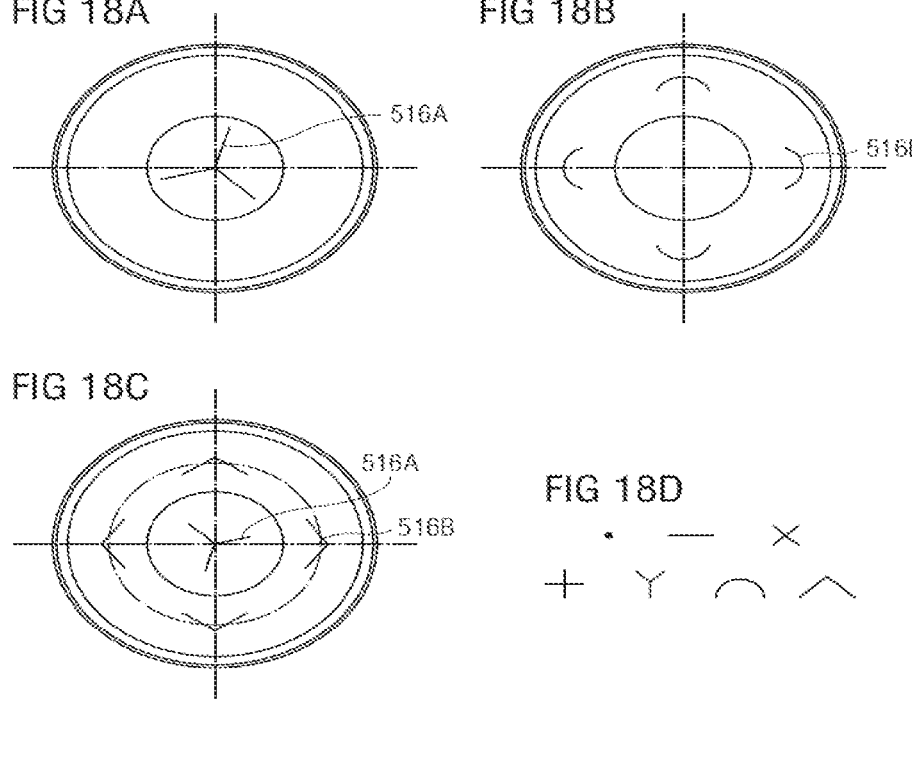

As shown in FIGS. 18A, 18B and 18C, the valve can comprise at least one slit 516 in the base surface 515. It is noted that the slits described herein may also be provided any other valve configurations, e.g. in tubular or dumbbell shaped valves, without the other features described for the valves in FIGS. 17A to 17F. Specifically, as shown in FIG. 18A, the valve can comprise at least one center slit 516A, The center slit 516A may have a Y shape, as shown in FIG. 18A. A center slit 516A can support the introduction of the needle in the valve and can be configured to seal once the needle is withdrawn. In one embodiment, there may be no flow through the center slit 516A.

Further, as shown in FIG. 18B, the valve can comprise at least one outer slit 516B. The at least one outer slit 516B can form an outer slit profile, for example made up by four slits at the same distance from the center of the valve, which may be have an arc shape, as shown in FIG. 18B. An outer slit 516B can contribute towards aspiratory flow, for instance while drawing blood using a syringe.

Further, as shown in FIG. 18C, the valve can comprise at least one center slit 516A and at least one outer slit 516B. For instance, the valve can comprise one center Y shaped slit and four V shaped slits at a same distance from the center slit, as shown in FIG. 18C.

As shown in FIG. 18D, the center slit 516A can have the form of a hole, a slit, a cross slit, a plus slit, a Y slit, an arc slit, a V slit, or any other shape. The center slit profile may vary with respect to the shape, size, or orientation of the slit. The center slit may be made in any way or process.

As shown in FIG. 18E, the outer slit may have the form of a slit, a T slit, a Y slit, a V slit, a rounded V slit, an arc slit, or any other shape. The outer slit profile may vary with respect to the shape, size, orientation, location or number of the at least one slit. The at least one outer slit may be made in any way or process. The valve may comprise any combination of a central slit and outer slits described above.

As shown in FIGS. 19A and 19B, the disc 500 already discussed further above may be joint or linked at a joint 500A to the valve. For instance, in connection with the specific valve configuration described in FIGS. 17A to 17F, the disc 500 may extend from the base surface in the direction of the peripheral wall 514 as shown in FIG. 19A, or may extend from the base surface in the opposite direction of the peripheral wall 514, to the outside of the valve, as shown in FIG. 19B. It is noted that the disc may be joint to any kind of valve, having a different configuration than shown in FIGS. 19A and 19B. For instance, the disc 500 may be joint to a valve having a dumbbell shape or a tubular shape, as discussed above. The disc 500 may be made of rigid, a semi-rigid or a soft material. The thickness, the shape and the size of the disc 500 may vary to optimize the function of the disc in stabilizing the valve and holding the valve in its position. The joint may be made by glue, welding, insert moulding or other means known to the skilled person.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth in the claims.

Accordingly, it is not intended that the scope of the foregoing description be limited to the exact description set forth above, but rather that such description be construed as encompassing such features that reside in the present invention, including all the features and embodiments that would be treated as equivalents thereof by those skilled in the relevant art.

The scope of the present invention herein disclosed is not limited by the particular disclosed embodiments described above but determined only by a fair reading of the appended claims.

LIST OF REFERENCE NUMERALS 410 intravenous catheter assembly
411*a* first fluid path
411*b* second fluid path
412 catheter hub
412*a* first part of catheter hub
412*b* second part of catheter hub
414 catheter tube
416 needle hub
418 distal wall
420 needle
422 distal end of catheter hub 412
422*b* distal end of second part 412*b*
422-1 distal end of second valve 473
422-2 distal end of upper part 482
422-3 distal end of first arm 440
422-4 distal end of second arm 422
424 proximal end of catheter hub 412
424-1 proximal end of plug 475
424-2 proximal end of catheter tube 414
426 needle guard
428 needle shaft
436 proximal section
438 stopping element
440 first arm
442 second arm
444 base portion
446 tension element
448 housing
450 distal end section 452 proximal end section
454 needle tip
456 inner surface/wall of catheter hub 412
456-2 inner surface/wall of upper part 482
456-3 inner surface/wall of needle hub housing 479
456-4 inner surface of housing 448
457 stepped surface of part 412*a*
458-1 outer wall/surface of second valve 473
458-2 outer wall/surface of catheter hub 412
458-3 outer wall/surface of upper part 482 and/or lower part 483
459 stepped surface of part 412*b*
460 distal side
461 slip ring
462 wings
463 distal section
464 port/port body
465 port opening/inlet
466 bore of the port
467 inner space of catheter housing
468 opening of the catheter housing
469 port/side port
470 sidewall of catheter housing
471 first valve
472 elastomeric septum of first valve
473 second valve
474 blood control septum of second valve
475 plug
476 chamber
477 opening of the catheter housing
478 needle guard casing
479 inner space/housing of needle hub
480 projection of catheter hub housing 448
480-1 projection of needle hub 416
480-2 projection of needle hub 416
482 groove of catheter hub housing 448
481-1 groove of needle hub 416
481-2 groove of needle hub 416
482 upper part
483 lower part
484 protrusion ring
485 ring groove
486 top portion
487 bottom portion
488 bore of needle guard casing
489 fitment
490 upper end of needle guard
491 lower end of needle guard
493 first disc like retaining protrusion
494 retaining depression
495 second disc like retaining protrusion
496 enlargement
497 opening
498 local depression
499 through-bore
500 disc
500A joint
501 cut
502 proximal needle feature
502A needle bend
502B needle crimp
502C needle pressing
503 needle fixation means
504 needle fixation means
505 wing alignment feature
505A wing alignment projection
505B wing alignment element

505C annular projection
505D annular recess
505E lateral projection
506 catheter hub alignment feature
506A wing base
506B wing socket
506C slot
506D indent
507 stopper element
508 needle guard engaging element
509 needle guard anti-rotation element
510 wing member
511 window
512 port hole
513 elastomeric member
514 peripheral wall
515 base surface
516 slit
516A center slit
516B outer slit
517 lateral annular protrusion
518 vertical annular projection
519 inner vertical projection
520 second vertical projection A axial direction

The invention claimed is:

1. An intravenous catheter assembly comprising:

a catheter tube;

a catheter hub having a distal end and a proximal end, wherein the distal end is joined to the catheter tube and the proximal end defines a housing having inner space;

a needle extending through the catheter hub and the catheter tube and defining an axial direction, wherein the needle has opposite proximal and distal ends, the distal end forming a needle tip, and the proximal end comprising a proximal needle feature, wherein the proximal needle feature comprises a deformation at the proximal end of the needle, and wherein the deformation comprises a needle bend, a needle crimp or a needle pressing;

a port extending outwardly in a direction perpendicular to the axial direction from a sidewall of the catheter hub;

a needle hub attached to the proximal end of the needle having a housing having an inner space, wherein the needle hub defines an aperture having two sections and wherein the two sections have different diameters, and wherein the deformation at the proximal end of the needle will restrict the proximal end of the needle from passing through the needle hub;

a needle guard comprising an upper end and a lower end, the needle guard slidably arranged on the needle and the upper end of the needle guard being securely retained in the housing of the catheter hub exposing the lower end of the needle guard and wherein in a ready to use position, an entire catheter hub portion with the lower end of the needle guard is securely retained in an inner space of the needle hub, and wherein the needle guard includes a base portion and first and second arms extending from the base portion, wherein the first arm is deflected radially outwards by the needle against a restoring force when the needle is in its ready position whereby the needle guard is brought into retaining contact with the catheter hub as long as the first arm is in its deflected state; and wherein the needle hub comprises a needle guard engaging element and the needle guard comprises a corresponding needle guard anti-rotation element configured to engage the needle guard engaging element to restrict rotation of the needle guard, wherein the needle guard engaging element comprises a rib extending from an inner wall of the needle hub housing towards the inner space of the needle hub housing.

2. The intravenous catheter assembly as claimed in claim 1, wherein an inner wall of the needle hub housing is provided with at least one projection and/or groove matching with at least one corresponding projection and/or groove provided in an outer wall of the catheter hub.

\* \* \* \* \*